United States Patent
Huang et al.

(10) Patent No.: US 12,377,094 B2
(45) Date of Patent: *Aug. 5, 2025

(54) THERAPEUTIC COMPOSITIONS AND METHODS FOR TREATING CHECKPOINT INHIBITOR-RESISTANT TUMORS USING PLINABULIN-BASED COMBINATION THERAPIES

(71) Applicant: BeyondSpring Pharmaceuticals, Inc., Florham Park, NJ (US)

(72) Inventors: Lan Huang, New York, NY (US); Ramon Mohanlal, New York, NY (US); James R. Tonra, New York, NY (US)

(73) Assignee: BeyondSpring Phamaceuticals, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/952,842

(22) Filed: Nov. 19, 2024

(65) Prior Publication Data

US 2025/0073231 A1    Mar. 6, 2025

Related U.S. Application Data

(63) Continuation of application No. 18/554,595, filed as application No. PCT/US2022/023793 on Apr. 7, 2022.

(60) Provisional application No. 63/214,010, filed on Jun. 23, 2021, provisional application No. 63/173,015, filed on Apr. 9, 2021.

(51) Int. Cl.
| | |
|---|---|
| *A61K 31/496* | (2006.01) |
| *A61K 31/337* | (2006.01) |
| *A61K 39/00* | (2006.01) |
| *A61K 39/395* | (2006.01) |
| *A61P 35/00* | (2006.01) |

(52) U.S. Cl.
CPC .......... *A61K 31/496* (2013.01); *A61K 31/337* (2013.01); *A61K 39/3955* (2013.01); *A61P 35/00* (2018.01); *A61K 2039/545* (2013.01)

(58) Field of Classification Search
CPC .............. A61P 35/00; A61K 2039/545; A61K 39/3955; A61K 31/337; A61K 31/496
See application file for complete search history.

(56) References Cited

U.S. PATENT DOCUMENTS

| | | | |
|---|---|---|---|
| 4,410,537 A | 10/1983 | Kneen | |
| 4,535,183 A | 8/1985 | Kneen | |
| 5,607,934 A | 3/1997 | Tone et al. | |
| 5,733,888 A | 12/1998 | Bryans et al. | |
| 5,852,018 A | 12/1998 | Bryans et al. | |
| 5,872,151 A | 2/1999 | Rhodes et al. | |
| 5,874,443 A | 2/1999 | Kiely et al. | |
| 5,886,210 A | 3/1999 | Rayle et al. | |
| 5,891,877 A | 4/1999 | Brocchini et al. | |
| 5,922,683 A | 7/1999 | Or et al. | |
| 5,939,098 A | 8/1999 | Reidenberg et al. | |
| 5,958,980 A | 9/1999 | Rhodes | |
| 6,069,146 A | 5/2000 | Fenical et al. | |
| 6,096,786 A | 8/2000 | Rhodes | |
| 6,350,759 B1 | 2/2002 | Casara et al. | |
| 6,358,957 B1 | 3/2002 | Fukumoto et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,583,143 B2 | 6/2003 | Haddach | |
| 6,713,480 B2 | 3/2004 | Fukumoto et al. | |
| 6,808,710 B1 | 10/2004 | Wood et al. | |
| 6,972,289 B1 | 12/2005 | Kanzaki et al. | |
| 7,026,322 B2 | 4/2006 | Hayashi et al. | |
| 7,064,201 B2 | 6/2006 | Hayashi et al. | |
| 7,488,802 B2 | 2/2009 | Collins et al. | |
| 7,629,380 B2 | 12/2009 | McMorris et al. | |
| 7,635,757 B2 | 12/2009 | Freeman et al. | |
| 7,674,903 B2 | 3/2010 | Hayashi et al. | |
| 7,700,615 B2 | 4/2010 | Edwards et al. | |
| 7,919,497 B2 | 4/2011 | Palladino et al. | |
| 7,935,704 B2 | 5/2011 | Palladino et al. | |
| 7,943,743 B2 | 5/2011 | Korman et al. | |
| 7,956,058 B2 | 6/2011 | Hayashi et al. | |
| 8,008,449 B2 | 8/2011 | Korman et al. | |
| 8,129,527 B2 | 3/2012 | Palladino et al. | |
| 8,168,757 B2 | 5/2012 | Finnefrock et al. | |
| 8,217,149 B2 | 7/2012 | Irving et al. | |
| 8,247,552 B2 | 8/2012 | Palladino et al. | |
| 8,618,292 B2 | 12/2013 | Palladino et al. | |
| 9,358,289 B2 | 6/2016 | Korman et al. | |
| 9,394,368 B2 | 7/2016 | Brogdon et al. | |
| 10,076,518 B2 | 9/2018 | Huang | |
| 10,155,748 B2 | 12/2018 | Huang et al. | |
| 10,238,630 B2 | 3/2019 | Cox et al. | |
| 10,238,650 B2 | 3/2019 | Huang | |

(Continued)

FOREIGN PATENT DOCUMENTS

| | | |
|---|---|---|
| CN | 110240592 | 9/2017 |
| EA | 010198 B1 | 6/2008 |

(Continued)

OTHER PUBLICATIONS

Hardin (Expert Opinion on Pharmacotherapy, 2017 vol. 18, No. 7, 701-716). (Year: 2017).*

(Continued)

*Primary Examiner* — Kortney L. Klinkel
*Assistant Examiner* — Richard Grant Peckham
(74) *Attorney, Agent, or Firm* — Knobbe Martens Olson & Bear LLP

(57) ABSTRACT

Disclosed herein are methods of treating, preventing or ameliorating a disease or condition associated with cancer or a tumor. In some embodiments, the method includes administering a compound of Formula (I) to a subject in need thereof wherein the cancer or the tumor is or becomes resistant to one or more immune checkpoint inhibitors.

22 Claims, 2 Drawing Sheets

(56) References Cited

U.S. PATENT DOCUMENTS

| | | |
|---|---|---|
| 10,357,491 B2 | 7/2019 | Huang |
| 10,550,104 B2 | 2/2020 | Huang et al. |
| 10,569,169 B2 | 2/2020 | Li et al. |
| 10,596,169 B2 | 3/2020 | Huang |
| 10,668,063 B2 | 6/2020 | Huang |
| 10,912,748 B2 | 2/2021 | Mohanlal |
| 11,045,467 B2 | 6/2021 | Huang |
| 11,229,642 B2 | 1/2022 | Huang et al. |
| 11,254,657 B2 | 2/2022 | Huang |
| 11,400,086 B2 | 8/2022 | Mohanlal et al. |
| 11,633,393 B2 | 4/2023 | Huang |
| 11,786,523 B2 | 10/2023 | Huang |
| 11,857,522 B2 | 1/2024 | Mohanlal et al. |
| 11,918,574 B2 | 3/2024 | Huang |
| 12,024,501 B2 | 7/2024 | Huang et al. |
| 2002/0028819 A1 | 3/2002 | Teng et al. |
| 2002/0143021 A1 | 10/2002 | Fukumoto et al. |
| 2004/0102454 A1 | 5/2004 | Hayashi et al. |
| 2004/0176372 A1 | 9/2004 | Suto et al. |
| 2006/0079534 A1 | 4/2006 | Kanzaki et al. |
| 2006/0167010 A1 | 7/2006 | Hayashi et al. |
| 2006/0223822 A1 | 10/2006 | Hayashi et al. |
| 2007/0293453 A1 | 12/2007 | Fisher et al. |
| 2008/0199485 A1 | 8/2008 | Kundig et al. |
| 2008/0255035 A1 | 10/2008 | Trieu et al. |
| 2009/0170837 A1 | 7/2009 | Gourdeau et al. |
| 2009/0317368 A1 | 12/2009 | Chen |
| 2012/0041070 A1 | 2/2012 | Shengfan et al. |
| 2012/0277251 A1 | 11/2012 | Palladino et al. |
| 2013/0131018 A1 | 5/2013 | Leblond et al. |
| 2013/0303481 A1 | 11/2013 | Marcus |
| 2014/0322275 A1 | 10/2014 | Brogdon et al. |
| 2014/0363514 A1 | 12/2014 | Koyakutty et al. |
| 2015/0202291 A1 | 7/2015 | Bosch et al. |
| 2015/0291549 A1 | 10/2015 | Chupak et al. |
| 2016/0243153 A1 | 8/2016 | Sundaram et al. |
| 2017/0226221 A1 | 8/2017 | Madiyalakan et al. |
| 2018/0028531 A1 | 2/2018 | Huang et al. |
| 2018/0140600 A1 | 5/2018 | Li et al. |
| 2019/0209549 A1 | 7/2019 | Arline et al. |
| 2020/0129504 A1 | 4/2020 | Mohanlal et al. |
| 2020/0281921 A1 | 9/2020 | Huang |
| 2021/0030843 A1 | 2/2021 | Mohanlal |
| 2021/0052583 A1 | 2/2021 | Hogberg et al. |
| 2021/0161888 A1 | 6/2021 | Huang et al. |
| 2021/0177952 A1 | 6/2021 | Mohanlal et al. |
| 2022/0378784 A1 | 12/2022 | Mohanlal et al. |
| 2022/0387365 A1 | 12/2022 | He |
| 2023/0035763 A1 | 2/2023 | Tonra |
| 2023/0181605 A1 | 6/2023 | Mohanlal et al. |
| 2024/0082243 A1 | 3/2024 | Huang |
| 2024/0197723 A1 | 6/2024 | Huang |
| 2024/0299377 A1 | 9/2024 | Mohanlal |
| 2024/0368126 A1 | 11/2024 | He |
| 2024/0408082 A1 | 12/2024 | Lloyd et al. |
| 2024/0425485 A1 | 12/2024 | Huang |
| 2025/0073230 A1 | 3/2025 | Huang et al. |

FOREIGN PATENT DOCUMENTS

| | | |
|---|---|---|
| EA | 016817 B1 | 7/2012 |
| EP | 0 054 924 | 6/1982 |
| EP | 0 655 060 | 1/1998 |
| GB | 2143823 | 2/1985 |
| JP | 05-9164 | 1/1993 |
| JP | 05-255106 | 10/1993 |
| JP | 10-130266 | 5/1998 |
| JP | 2002-507612 A | 3/2002 |
| JP | 2012-144512 | 8/2012 |
| JP | 2013-501791 | 1/2013 |
| JP | 2014-508167 | 4/2014 |
| JP | 2015-030679 | 2/2015 |
| JP | 2016-516523 | 6/2016 |
| JP | 2016-518879 | 6/2016 |
| JP | 2018-036233 | 3/2018 |
| JP | 2020-189806 | 11/2020 |
| RU | 2258702 | 8/2005 |
| RU | 2011 148 945 A | 4/2010 |
| WO | WO 87/05297 | 9/1987 |
| WO | WO 94/07479 | 4/1994 |
| WO | WO 95/06077 | 3/1995 |
| WO | WO 95/21832 | 8/1995 |
| WO | WO 96/20190 | 7/1996 |
| WO | WO 99/38844 | 8/1999 |
| WO | WO 99/048889 | 9/1999 |
| WO | WO 00/012121 | 3/2000 |
| WO | WO 01/053290 | 7/2001 |
| WO | WO 01/070663 | 9/2001 |
| WO | WO 03/074550 | 9/2003 |
| WO | WO 03/097164 | 11/2003 |
| WO | WO 04/016600 | 2/2004 |
| WO | WO 04/054498 | 7/2004 |
| WO | WO 04/093831 | 11/2004 |
| WO | WO 05/077940 | 8/2005 |
| WO | WO 06/121168 | 11/2006 |
| WO | WO 07/035841 | 3/2007 |
| WO | WO 07/113648 | 10/2007 |
| WO | WO 08/128169 | 10/2008 |
| WO | WO 09/064444 | 5/2009 |
| WO | WO 09/089260 | 7/2009 |
| WO | WO 10/001169 | 1/2010 |
| WO | WO 10/083439 | 7/2010 |
| WO | WO 10/101627 | 9/2010 |
| WO | WO 11/034954 | 3/2011 |
| WO | WO 11/050344 | 5/2011 |
| WO | WO 11/066389 | 6/2011 |
| WO | WO 11/079507 | 7/2011 |
| WO | WO 11/109625 | 9/2011 |
| WO | WO 11/146382 | 11/2011 |
| WO | WO 11/151423 | 12/2011 |
| WO | WO 12/014549 | 2/2012 |
| WO | WO 12/035436 | 3/2012 |
| WO | WO 12/074904 | 6/2012 |
| WO | WO 12/145493 | 10/2012 |
| WO | WO 13/078537 | 6/2013 |
| WO | WO 13/090552 | 6/2013 |
| WO | WO 13/177633 | 12/2013 |
| WO | WO 14/036412 | 3/2014 |
| WO | WO 14/066834 | 5/2014 |
| WO | WO 14/130657 | 8/2014 |
| WO | WO 14/160183 | 10/2014 |
| WO | WO 14/183066 | 11/2014 |
| WO | WO 14/195852 | 12/2014 |
| WO | WO 15/069770 | 5/2015 |
| WO | WO 15/069790 | 5/2015 |
| WO | WO 15/160641 | 10/2015 |
| WO | WO 16/081281 | 5/2016 |
| WO | WO 16/165007 | 10/2016 |
| WO | WO 17/062505 | 4/2017 |
| WO | WO 21/225908 | 11/2021 |

OTHER PUBLICATIONS

Tagliamento (Expert Opinion on Investigational Drugs 2019, vol. 28, No. 6, 513-523) (Year: 2019).*

Washington (Nivolumab and Plinabulin in Treating Patients With Stage IIIB-IV, Recurrent, or Metastatic Non-small Cell Lung Cancer , NCT02846792, Last Updated Mar. 4, 2019, 1-6). (Year: 2019).*

"Definition of 'within'". [Online] [2015 Archived version accessed on Aug. 13, 2020 from https://web.archive.org/web/20151030162428/ https://dictionary.cambridge.org/us/dictionary/english/within. Cambridge English Dictionary. (Year: 2015).

Abels, Christoph, Targeting of the Vascular System of Solid Tumours by Photodynamic Therapy (PDT), Photochem Photobiol Sci., (Mar. 2004) 3: 765-771.

Abolhasani et al., Jan. 2015, In-silico investigation of tubulin binding modes of a series of novel antiproliferative spiroisoxazoline compounds using docking studies, Iranian Journal of Pharmaceutical Research, 14(1):141-147.

Abstracts of The 1999 Joint Chubu and Kansai Branch Conference and Symposia of Japan Society for Bioscience, Biotechnology, and Agrochemistry, (1999) p. 48.

(56) References Cited

OTHER PUBLICATIONS

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.
Agarwal et al., "OP449, a Novel SET Antagonist, is Cytotoxic to Leukemia Cells and Enhances Efficacy of Tyrosine Kinase Inhibitors in Drug-Resistant Myeloid Leukemias," pursuant to an EMBASE record for a Conference ABSTRACT: 603. Oncogenes and Tumor Suppressors: Poster II (Nov. 15, 2013) Blood (2013) 122(21): 2511.
Aggarwal et al., Antiangiogenic agents in the management of non-small cell lung cancer: Where do we stand now and where are we headed? Cancer Biology & Therapy (2012), 13(5), 247-263.
Ahmed et al. "A new rapid and simple non-radioactive assay to monitor and determine the proliferation of lymphocytes: an alternative to [$^3$H]thymidine incorporation assay." J. Immunol. Methods. 170, 211-224 (1994).
Akerlund et al., "Diketopiperazine-Based Polymers from Common Amino Acids," Journal of Applied Polymer Science, (2000) 78 (12), 2213-2218.
Algaier et al. "The effects of dimethyl sulfoxide on the kinetics of tubulin assembly." Biochim. Biophys. Acta. 954, 235-43 (1988).
Ali et al. "Toxicity of echinulin from Aspergillus chevalieri in rabbits." Toxicology Letters. (1989) 48:235-41.
Asahina, T., "Spectrochemical Study of Amino-acid Anhydrides," Bulletin of the Chemical Society of Japan, (1930) 5, 354-365.
Augustin, M. "Die Umsetzung des 2,5-Diketopiperazins mit Aldehyden und Nitrosoverbindungen" Journal für Praktische Chemie, (1966) 32(4), 158-166.
Aviel-Ronen et al., "K-ras Mutations in Non-Small-Cell Lung Carcinoma: A Review," *Clinical Lung Cancer* (Jul. 2006) vol. 8, No. 1, pp. 30-38.
Bankowska et al., Derivatives of 1,2,3-triazole. Potential drugs?, Wiadomosci Chemiczne (2012), 66(11-12), 993-1022.
Bauer et al., Jan. 15, 2010, Identification of markers of taxane sensitivity using proteomic and genomic analyses of breast tumors from patients receiving neoadjuvant paclitaxel and radiation, Clinical Cancer Research, 16(2):681-690.
Bazhenova, Feb. 21, 2021, Nivolumab in Combination With Plinabulin in Patients With Metastatic Non-Small Cell Lung Cancer (NSCLC), ClinicalTrials.gov, NCT02812667 version 7.
Beavis et al., "Dual PD-1 and CTLA-4 Checkpoint Blockade Promotes Antitumor Immune Responses through CD4$^+$Foxp$^3$-Cell-Mediated Modulation of CD103$^+$ Dendritic Cells," Cancer Immunol Res (Sep. 2018) 6(9):1069-1081.
Berenbaum, Jun. 1989, What is synergy?, Pharmacol. Rev., 41(2):93-141.
Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.
Bertelsen et al., "Vascular effects of plinabulin (NPI-2358) and the influence on tumour response when given alone or combined with radiation," International Journal of Radiation Biology (2011), 87(11), 1126-1134.
Bertino J., et al., "Principles of Cancer Therapy." Cecil Textbook of Medicine. Eds. Lee Goldman, et al. 21nd ed., (2000), Chapter 198, pp. 1060-1074.
Bigioni et al., Sep. 2008, Antitumour effect of combination treatment with Sabarubicin (MEN 10755) and cis-platin (DDP) in human lung tumour xenograft, Cancer Chemother. Pharmacol., 62(4):621-629.
Blankenstein et al., Mar. 1, 2012, The determinants of tumour immunogenicity, Nat. Rev. Cancer, 12(4):307-313.
Blayney et al., "Plinabulin, a Novel Small Molecule That Ameliorates Chemotherapy-Induced Neutropenia, is Administered on the Same Day of Chemotherapy and Has Anticancer Efficacy", Meeting Info.: 58th Annual Meeting and Exposition of the American Society-of-Hematology (ASH), Blood (2016) 128(22): 2508.
Bond et al. "The Synthesis of Viridamine, a Penicillium Viridicatum Mycotoxin." Synthetic Commun. 19 (13&14), 2551-2566 (1989).

Borisy, G.G. "A Rapid Method for Quantitative Determination of Microtubule Protein using DEAE-Cellulose Filters." Anal. Biochem. 50, 373-385 (1972).
Braga et al. "Crystal Polymorphism and Multiple Crystal Forms," Struct Bond (2009) 132:25-50.
Brahmer et al., "Safety and Activity of Anti-PD-L1 Antibody in Patients with Advanced Cancer," N Engl J Med (2012) 366:2455-2465.
Buchbinder et al., Feb. 2016, CTLA-4 and PD-1 pathways: similarities, differences, and implications of their inhibition, American Journal of Clinical Oncology, 39(1):98-106.
Burtles, Sally, "Transition from Preclinical to first-in-man Phase", Expert Scientific Group on Phase One Clinical Trials Final Report, Presentation Jun. 19, 2006, pp. 35-38.
Cai, Small molecule vascular disrupting agents: potential new drugs for cancer treatment, a 2009 update, Frontiers in Anti-Cancer Drug Discovery (2010), 1, 380-427.
Cai, Sui X., "Small Molecule Vascular Disrupting Agents: Potential New Drugs for Cancer Treatment", Recent Pat Anticancer Drug Discov. (2007) 2(1): 79-101.
Caira, 1998, Crystalline polymorphism of organic compounds, Topics in Current Chemistry, 198:163-208.
Callahan et al., "At the Bedside: CTLA-4- and PD-1-blocking antibodies in cancer immunotherapy", J Leukocyte Biol, vol. 94, Jul. 2013, pp. 41-53.
Carter et al., "No patient left behind: The promise of immune priming with epigenetic agents," Oncoimmunology (2017) vol. 6, No. 10, e1315486 (13 pages).
Champiat et al., Feb. 2014, Incorporating immune-checkpoint inhibitors into systemic therapy of NSCLC, J. Thorac. Oneal., 9(2):144-153.
Chang et al., 1998, Changing residue 338 in human factor IX from arninine to alanine causes an increase in catalytic activity, J. Biol. Chem., 272(9):4929-4936.
Chaplin et al., "Antivascular approaches to solid tumour therapy: evaluation of tubulin binding agents", Br. J. Cancer 1996, 74 (Suppl. XXVII), S86-S88.
Chen et al., "Adjuvant effect of docetaxel on the immune responses to influenza A H1N1 vaccine in mice," BMC Immunology (2012) 13:36, pp. 1-12.
Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.
Clezardin et al., Jan. 1, 2011, Bisphosphonates' antitumor activity: an unravelled side of a multifacted drug class, Bone, 48(1):71-79.
ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltrials.gov/ct2/show/NCT00892931> 7 pages.
ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from internet on Sep. 17, 2019], <URL: https://clinicaltrials.gov/ct2/show/NCT02846792?term=plinabuilin&rank=1> 11 pages.
ClinicalTrials.gov Identifier NCT03294577, "Plinabulin vs. pegfilgrastim in prevention of TAC induced neutropenia" (Sep. 27, 2107). <URL:ttps://clinicaltrials.gov/ct2/show/NCT3294577> 4 pp.
Clinicaltrials.gov, NCT00151073, Estramustine, docetaxel and zoledronate treatment in hormone-refractory adenocarcinoma of the prostate, https//clinicaltrials.gov/ct2/show/NCT00151073?term=zoledronate%2C+tubulin&draw=2&rank=1.
Cole, P., "Durvalumab, Human anti-PD-L1 monoclonal antibody Immune checkpoint inhibitor Oncolytic", Drugs of the Future 2014, 39(12): pp. 843-847.
Collins et al., 2014, Lipid tucaresol as an adjuvant for methamphetamine vaccine development, CHemComm, 50:4079-4081.
Cooper et al., "Response to BRAF Inhibition in Melanoma is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.

(56) References Cited

OTHER PUBLICATIONS

Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.
Crawford, Aug. 2003, Once-per-cycle pegilgrastim (neulata) for the management of chemotherapy-induced neutropenia, Seminars in Oncology 30(4)Suppl 13:23-30.
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).
Cui et al. "Novel Mammalian Cell Cycle Inhibitors, Tryprostatins A, B and Other Diketopiperazines Produced by Aspergillus fumigatus." J. Antibiotics. 49(6): 527-33 (1996).
Dale, Oct. 2015, Neutropenia, John Wiley & Sons Ltd., www.els.net, 8 pp.
Dalgleish, 2015, Rationale for combining immunotherapy with chemotherapy, Immunotherapy, 7(3):309-316.
Das et al., Feb. 1, 2015, Combination therapy with anti-CLTA4 and antiPD1 leads to distinct immunologic changes in-vivo, J. Immunolog, 194(3):950-959.
Davies, Feb. 3, 2014, New modalities of cancer treatment for NSCLC: focus on immunotherapy, Cancer Manag. Res., 6:63-75.
Davis et al., ZD6126: A Novel Vascular-targeting Agent That Causes Selective Destruction of Tumor Vasculature, Cancer Research (Dec. 15, 2002) 62: 7247-7253.
Dennis, Aug. 17, 2006, Off by a whisker, Nature, 442:739-741.
Dorwald, F., "Side Reactions in Organic Synthesis" Wiley-VCH Verlag Gmbh & Co. KgaA, Weinheim, (2005), book cover and preface p. IX only.
Drug Approval and Licensing Procedures in Japan 2001, 2001, pp. 243-244.
Du et al., Jul. 2018, docetaxel increases the risk of severe infections in the treatment of non-small cell lung cancer: a meta-analysis, Oncoscience, 5(7-8):220-238.
Duarte et al., 2022, Evaluation of synergism in drug combinations and reference models for future orientations in oncology, Curr. Res. Pharmacol. Drug Discov., 3:100110; pp. 1-13.
Dunitz et al., "Disappearing Polymorphs," Acc. Chem. Res. (1995) vol. 28, No. 4, pp. 193-200.
Dyson, Feb. 16, 2017, 4 Clinical Pearls for Granulocyte Colony Stimulating Factors (G-CSFs), Pharmacy Times, retrieved from the internet at URL <https://www.pharmacytimes.com/view/4-clinical-pearls-for-granulocyte-colony-stimulating-factors-g-csfs>, (retrieved on Dec. 11, 2023), Feb. 16, 2017.
El-Kenawi et al., Oct. 2013, Angiogenesis inhibitors in cancer therapy: mechanistic perspective on classification and treatment rationales, Br. J. Pharmacol., 170(4):712-729.
Elliott et al., Oct. 15, 1989, Sequence and schedule-dependent synergy of trimetrexate in combination with 5-fluorouracil in vitro and in mice, Cancer Res., 49(20):5586-5590.
Fan et al., 2021, Immunotherapy in colorectal cancer; current achievements and future perspective, Int. J. Biol. Sci., 17(14):3837-3849.
Fernandez-Medarde et al., Mar. 2011, Ras in cancer and developmental diseases, Genes & Cancer, 2(3):344-358.
Fernandez-Tejada et al., 2014, Design, synthesis, and immunologic evaluation of vaccine adjuvant conjugates based on QS-21 and tucaresol, Bioorganic & Medicinal Chemistry, 22:5917-5923.
Fernandez-Tejada et al., 2016, Development of improved vaccine adjuvants based on the saponin natural product QS-21 through chemical synthesis, Accounts of Chemical Research 49:1741-1756.
Ferrer et al., Plinabulin: tubulin polymerization inhibitor vascular-disrupting agent oncolytic, Drugs of the Future (2010), 35(1), 11-15.
Fessas et al., 2017, A molecular and preclinical comparsion of the PC-1-targeted t-cell checkpoint inhibitors nivolumab and mebrolizumag, Seminars in Oncology, 44:136-140.
Field et al., 2014, Microtubule-targeting agents are clinically successful due to both mitotic and interphase impairment of microtubule function, Bioorganic & Medicinal Chemistry, 22:5050-5059.
Flanigan et al., Jan. 7, 2011, Melanoma brain metasteses: is it time ro reassess the bias?, Current Problems in Cancer, 35(4):200-210.
Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.
Folkman, Dec. 2002, Role of angiogenesis in tumor growth and metastasis, Semin Oncol, 29:15-18.
Friedman et al., 2000, Schedule-dependent activity of irinotecan plus BCNU against malignant glioma xenografts, Cancer Chemother. Pharmacol., 45(4):345-349.
Frost et al., Novel Syngeneic Pseudo-orthotopic Prostate Cancer Model: Vascular, Mitotic and Apoptotic Responses to Castration, Microvasc Research (Dec. 2004) 69: 1-9.
Fukushima et al., "Biological Activities of Albonoursin," J. Antibiotics, (1973) 26:175.
Gallina et al., "Condensation of 1,4-diacetylpiperazine-2,5-dione with aldehydes", Tetrahedron 1974, 30, 667-673.
Gameiro et al., "Exploitation of differential homeostatic proliferation of T-cell subsets following chemotherapy to enhance the efficacy of vaccine-mediated antitumor responses," Cancer Immunology Immunotherapy (2011) vol. 60, No. 9, pp. 1227-1242.
Garcia-Fuente et al., 2018, CISNA: an accurate description of dose-effect and synergism in combination therapies, Sci. Rep., 8:4964; pp. 1-9.
Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).
Glisson et al., 2002, Phase II trial of docetaxel and cisplatin combination chemotherapy in patients with squamous cell carcinoma of the head and neck, Journal of Clinical Oncology 20:1593-1599.
Goldani et al. "Treatment of murine pulmonary mucormycosis with SCH 42427, a broad-spectrum triazole antifungal drug", Correspondence, J Antimicrob Chemother. 33, 369-372 (1994).
Goldfarb et al., "Synthesis of β-2-thienylalanine," Izvestiya Akademii Nauk SSSR, Seriya Khimicheskaya, (1958) 98-100, as abstracted by CAPLUS.
Gordon et al. "Reductive Alkylation on a Solid Phase: Synthesis of a Piperazinedione Combinatorial Library." J. Bioorg. Med. Chem. Letters. 5, 47-50 (1995).
Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4):1021-1025.
Gridelli et al., Vascular disrupting agents: a novel mechanism of action in the battle against non-small cell lung cancer, Oncologist (2009), 14(6), 612-620.
Gu et al., "Identification of CTLA-4 isoforms produced by alternative splicing and their association with myasthenia gravis," Clinical Immunology (Sep. 2008) vol. 128, Issue 3, pp. 374-381.
Gura, Trisha, "Cancer Models: Systems for Identifying New Drugs are Often Faulty", Science 7(Nov. 1997) 278(5340): 1041-1042.
Hamel, E. "Antimitotic Natural Products and Their Interactions with Tubulin." Med. Res. Rev. (1996) 16(2): 207-31.
Hartwell et al. "Checkpoints: Controls that Ensure the Order of Cell Cycle Events." Science. 246, 629-34 (1989).
Hayakawa, Structure-activity relationship analysis, Japanese Journal of Cancer and Chemotherapy, (2004), 31(4):526-528.
Hayashi et al., "Total Synthesis of Anti-microtubule Diketopiperazine Derivatives: Phenylahistin and Aurantiamine," J. Org. Chem., (2000) 65: 8402-8405.
Hayashi et al., Medicinal chemistry and chemical biology of diketopiperazine-type antimicrotubule and vascular-disrupting agents, Chemical & Pharmaceutical Bulletin (2013), 61(9), 889-901.
Hayashi et al., Small peptide-based medicinal chemistry for intractable disease, Peptide Science (2009), Volume Date 2008, 45th, 139-140.
He et al., "Low-dose paclitaxel enhances the anti-tumor efficacy of GM-CSF surface-modified whole-tumor-cell vaccine in mouse model of prostate cancer," Cancer Immunology Immunotherapy (2011) vol. 60, No. 5, pp. 715-730. Abstract.
Heist et al., "Abstract C30: Phase 1/2 study of the vascular disrupting agent (VCA) plinabulin (NPI-2358) combined with docetaxel in

(56) References Cited

OTHER PUBLICATIONS patients with non-small cell lung cancer (NSCLC)," Mol. Cancer Ther., 2009; 8(12 Suppl):C30, 2 pages.
Heist et al., "Randomized Phase 2 Trial of Plinabulin (NPI-2358) Plus Docetaxel in Patients with Advanced Non-Small Lung Cancer (NSCLC)," 2014 ASCO Annual Meeting. . . (abstr 8054) Poster Presentation. Retrieved from the internet Jul. 17, 2017: <http://meetinglibrary.asco.org/record/92548/poster>.
Helleman et al. "The International Journal of Biochemistry & Cell Biology," vol. 42, pp. 25-30 (2010).
Hellmann et al., May 31, 2018, Nivolumab plus ipilimumab in lung cancer with a high tumor mutational burden, N. Engl. J. Med., 378(22):2093-2104.
Hellmann et al., Nov. 21, 2019, Nivolumab plus ipilimumab in advanced non-small-cell lung cancer, The New England Journal of Medicine, 381:2020-2031.
Hodi et al., Nov. 2016, Combined nivolumab and ipilimumab versus ipilimumab alone in patients with advanced melanoma: 2-year overall survival outcomes in a multicentre, randomised, controlled, phase 2 trial, Lancet Oncol., 17:1558-1568.
Horak et al. "Structures of the Austalides A-E, Five Novel Toxic Metabolites from Aspergillus ustus." J Chem Soc Chem Commun. (1981) 1265-67.
Http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).
Hursthouse et al., "Why Do Organic Compounds Crystallise Well or Badly or Ever so Slowly? Why is Crystallisation Nevertheless Such a Good Purification Technique?," Organic Process Res & Devel (2009) vol. 13, No. 6, pp. 1231-1240.
Hwang et al., 2019, Heat shock proteins: a dual carrier-adjuvant for an anti-drug vaccine against heroin, Bioorganic & Medicinal Chemistry, 27:125-132.
Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.
Intlekofer et al., Jul. 2013, At the bench: preclinical rationale for CTLA-4 and PD-1 blockade as cancer immunotherapy, J. Leukoc Biol., 94(1):25-39.
Ishibashi et al., Sep. 1989, Interleukin-6 is a potent thrombopoietic factor in vivo in mice, Blood, 74(4):1241-1244.
Iwasaki, S. "Antimitotic Agents: Chemistry and Recognition of Tubulin Molecule." Med Res Rev. (1993) 13: 183-198.
Iwasaki, S. "Bioactive Natural Products Interfering with Microtubule Function." Kagaku to Seibutsu. 32(3): 153-159 (1994).
Januchowski et al., Jan. 2014, Microarray-based detection and expression analysis of extracellular matrix proteins in drug-resistant ovarian cancer cell lines, Oncology Reports, 32:1981-1990.
Ji et al., Tubulin Colchicine Binding Site Inhibitors as Vascular Disrupting Agents in Clinical Developments, Current Medicinal Chemistry (2015), 22(11), 1348-1360.
Jiang et al., "A Novel Peptide Isolated from a Phage Display Peptide Library with Trastuzumab Can Mimic Antigen Epitope of HER-2*," (Feb. 11, 2005) J Biol Chem, vol. 280, No. 6, pp. 4656-4662.
Jin et al., Feb. 28, 2022, Different syngeneic tumors show distinctive intrinsic tumor-immunity and mechanisms of actions (MOA) of anti-PD-1 treatment, Sci. Rep., 12: 3278, pp. 1-18.
Johnson et al. "Kinetic Analysis of Microtubule Self-assembly in Vitro." J. Mol. Biol. 117, 1-31 (1977).
Jure-Kunkel M. et al., "Synergy between chemotherapeutic agents and CTLA-4 blockade in preclinical tumor models", Cancer Immunol. Immunother. 2013, vol. 62, pp. 1533-1545.
Kakoulidou et al., "Human Soluble CD80 is Generated by Alternative Splicing, and Recombinant Soluble CD80 Binds to CD28 and CD152 Influencing T-cell Activation," Scandinavian J. Immunol (Nov. 2007) 66(5):529-537.
Kamb, Alexander, "What's wrong with our cancer models?", Nature Reviews Drug Discovery (Feb. 2005) 4: 161-165.

Kanoh et al., "(−)- Phenylahistin: A New Mammalian Cell Cycle Inhibitor Produced by Aspergillus USTUS," Bioorganic & Medicinal Chemistry Letters, (1997) 7: 2847-2852.
Kanoh et al., "(−)-Phenylahistin Arrests Cells in Mitosis by Inhibiting Tubulin Polymerization," The Journal of Antibiotics, (1999) 52: 134-141.
Kanoh et al., "Antitumor Activity of Phenylahistin in Vitro and in Vivo," Bioscience Biotechnology Biochemistry, (1999) 63(6): 1130-1133.
Kanoh et al., "Synthesis and Biological Activities of Phenylahistin Derivatives," Bioorganic & Medicinal Chemistry, (1999) 7: 1451-1457.
Kanojia et al., May 2015, βIII-tubulin regulates breast cancer meastases to the brain, Mol Cancer Ther., 14(5):1152-1161.
Kanthou et al., Microtubule depolymerizing vascular disrupting agents: novel therapeutic agents for oncology and other pathologies, International Journal of Experimental Pathology(2009), 90(3), 284-294.
Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12):1042-1047.
Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.
Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.
Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.
Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).
Kanzaki et al., "Novel Cyclic Dipeptide Dehydrogenase and Assay Method for Its Activity," Scientific Reports of the Faculty of Agriculture, Okayama University, (1999) 88: 7-11.
Kashyap et al., Sep. 24, 2019, GEF-H1 signaling upon microtubule destabilization is required for dendritic cell activation and specific anti-tumor responses, Cell Reports, 28:3367-3380.
Keepers et al. "Comparison of the Sulforhodamine B Protein and Tetrazolium (MTT) Assays for in vitro Chemosensitivity Testing." Eur. J. Cancer. 27, 897-900 (1991).
Kim et al. "Polymer attached cyclic peptides, tetrahedron: Asymmetry." 3(11):1421-1430 (1992).
Kingston, Correction to Tubulin-interactive natural products as anticancer agents, Journal of Natural Products (2011), 74(5), 1352.
Kingston, Tubulin-Interactive Natural Products as Anticancer Agents, Journal of Natural Products (2009), 72(3), 507-515.
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3: 711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones1a," The Journal of Organic Chemistry, (1967) 33: 862-864.
Kreamer K., "Immune checkpoint blockade: A New Paradigm in Treating Advanced Cancer", J. Adv. Pract. Oncol., 2014, vol. 5, pp. 418-431.
Krendel et al., Apr. 2002, Nucleotide exchange factor GEF-H1 mediates cross-talk between microtubules and the actin cytoskeleton, Nature Cell Biology, 4:294-301 and supplementary information.
Krishan, A. "Rapid Flow Cytofluorometric Analysis of Mammalian Cell Cycle by Propidium Iodide Staining." J. Cell Biol. 66, 188-193 (1975).

(56) References Cited

OTHER PUBLICATIONS

Kupchan et al. "Steganacin and Steganangin, Novel Antileukemic Lignan Lactones from Steganotaenia araliacea 1-3." J. Am. Chem. Soc. (1973) 95(4): 1335-36.
Küster & Koeppenhöfer, "Über eininge Pyrrolderivate," Z. Physiol, Chem., (1927) 172:126-137.
Kwon et al., Apr. 2013, Mouse models for lung cancer, Mol. Oneal., 7(2):165-177.
La-Beck, 2021, Repurposing amino-bisphosphonates by liposome formulation for a new reole in cancer treatment, Seminars in Cancer Biology, 68:175-185.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (and how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., "A practical guide to pharmaceutical polymorph screening & selection," Asian Journal of Pharmaceutical Sciences (2014) vol. 9, pp. 163-175.
Lee et al., Colchicine site inhibitors of microtubule integrity as vascular disrupting agents, Drug Development Research (2008), 69(6), 352-358.
Li et al., May-Jun. 2017, Epitope mapping reveals the binding mechanism of a functional antibody cross-reactive to both human and murine programmed death 1, MABS, 9(4):628-637.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liao et al., "Design and synthesis of novel soluble 2,5-diketopiperazine derivatives as potential anticancer agents," European J Med Chem (2014) 83:236-244.
Liou et al., Aug. 12, 2004, Concise synthesis and structure-activity relationships of combretastatin A-4 analogues, 1-aroylindoles and 3-aroylindoles, as novel classes of potent antitubulin agents, Journal of Medicial Chemstry, 47(17):4247-4257.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liu et al., Dec. 31, 2019, Spectrum of EGFR aberrations and potential clinical implications, insights from integrative pan-cancer analysis, Cancer Communications, 40(1):43-59.
Liwo et al. "Origin of the Ring-Ring Interaction in Cyclic Dipeptides Incorporating an Aromatic Amino Acid." Tetrahedron Lett. 26, 1873-1876 (1985).
Lloyd et al. Dec. 2003, NPI-2358 and 2386: two new vascular/tubulin modifying agents greatly potentiate standard chemotherapy in xenograft models, Clin. Cancer Res., 9 6153s; Abstract #B59, 1 p.
Lloyd et al., 2015, Abstract A184: Activity of plinabulin in tumor models with kras mutations, Mol. Can. Thera. 14(12):Suppl. 2.
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Lu et al., Nov. 2012, An overview of tubulin inhibitors that interact with the colchicine binding site, Pharmaceutical Research, 29(11):2943-2971.
Luduena, R.F. "Contrasting Roles of Tau and Microtubule-associated Protein 2 in the Vinblastine-induced Aggregation of Brain Tubulin." J. Biol. Chem. 259:12890-98 (1984).

Lyman et al., "Risk Models for Predicting Chemotherapy-Induced Neutropenia," The Oncologist (2005) 10:427-437.
Lyman, 2011, Neutropenia, Encyclopedia of Cancer, pp. 2506-2509.
Lynch et al., "Ipilimumab in Combination With Paclitaxel and Carboplatin as First-Line Treatment in Stage IIIB/IV Non-Small-Cell Lung Cancer: Results From a Randomized, Double-Blind, Multicenter Phase II Study," (Jun. 10, 2012) J Clin Oncol, vol. 30, No. 17, pp. 2046-2054.
Mahindroo et al., "Antitubulin Agents for the Treatment of Cancer—A Medicinal Chemistry Update", Expert Opin. Ther. Patents (2006) 16(5): 647-691.
Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.
Malhotra, J., "A Phase I/II Study of Nivolumab, Ipilimumab and Plinabulin in Patients With Recurrent Small Cell Lung Cancer", ClinicalTrials.gov, NCT03575793 version 9, Apr. 15, 2020, <URL: https://clinicaltrials.gov/ct2/history/NCT03575793?V_9= View#StudyPageTop>.
Malhotra, J., Abstract 8570: "A phase I trial of plinabulin in combination with nivolumab and ipilimumab in patients with relapsed small cell lung cancer (SCLC): Big Ten Cancer Research Consortium (BTCRC-LUN17-127) study", Journal of Clinical Oncology, vol. 39, No. 15, May 28, 2021, DOI: 10.1200/JCO.2021.39.15_suppl.8570.
Martin et al., Sep. 2014, The microtubule-depolymerizing agent ansamitocin P3 programs dendritic cells toward enhanced anti-tumor immunity, Cancer Immunol. Immunother., 63(9):925-938.
Massarelli et al., Feb. 2014, Immunotherapy in lung cancer, Transl. Lung Cancer Res., 3(1):53-63.
Matsuda et al., "Pilot study of WT1 peptide-pulsed dendritic cell vaccination with docetaxel in esophageal cancer," Oncology Letters (Jul. 2018) vol. 16, No. 1, pp. 1348-1356.
Mazza et al., 2017, Treating EGFR mutation resistance in non-small cell lung cancer—role of osimertinib, The Application of Clinical Genetics, 10:49-56.
Melero et al., Aug. 2015, Evolving synergistic combinations of targeted immunotherapies to combat cancer, Nature Reviews Cancer, 15:457-472.
Millward et al., "Phase I trial of NPI-2358 (a novel vascular disrupting agent) plus docetaxel," J. Clin. Oncol. (May 2009) 27(15S): 3571-3571, Abstract.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2011), 30(3), 1065-1073.
Mita et al., "Phase 1 First-in-Human Trial of the Vascular Disrupting Agent Plinabulin (NPI-2358) in Patients with Solid Tumors or Lymphomas," Clinical Cancer Research (2010), 16(23), 5892-5899.
Mita et al., "Phase II study of docetaxel with or without plinabulin (NPI-2358) in patients with non-small cell lung cancer (NSCLC)", J. Clin. Oncol., 2010, vol. 28, No. 15 supplement. Abstract 7592, 2 pages.
Mita et al., Randomized Phase 2 Study of Docetaxel +/− Plinabulin (NPI-2358) in Patients with Non-Small Cell Lung Cancer (NSCLC), *Poster Presentation at ACS Annual '10 Meeting* (Jun. 4-8, 2010) 1 page.
Mitsudomi et al., "Mutations of ras genes distinguish a subset of non-small-cell lung cancer cell lines from small-cell lung cancer cell lines," *Oncogene* (Aug. 1991) vol. 6, No. 8, pp. 1352-1362.
Mizumoto et al., Nov. 1, 2005, Discovery of novel immunostimulants by dendritic-cell-based functional screening, Blood, 106(9):3082-3089.
Mohanlal et al., "The plinabulin/docetaxel combination to mitigate the known safety concerns of docetaxel," J Clin Oncol (2016) 34(15_suppl), Abstract e20595.
Mohanlal et al., Feb. 10, 2018, Plinabulin, a novel small molecule clinical stage 10 agent with anti-cancer activity, to prevent chemo-induced neutropenia and immune related AEs, Journal of Clinical Oncology, 36(5 Suppl):126.

(56) References Cited

OTHER PUBLICATIONS

Mohanlal et al., Mar. 1, 2017, Plinabulin as a novel small molecule clinical stage immuno-oncology agent for NSCLC, Journal of Clinical Oncology, 35(7), Supplement 1, Abstract 139.

Muguruma et al., 2016, Novel Hybrid Compound of a Plinabulin Prodrug with an IgG Binding Peptide for Generating a Tumor Selective Noncovalent-Type Antibody-Drug Conjugate; Bioconjugate Chem. 27(7):1606-1613.

Muguruma et al., OP-20: "Application of Fc-selective Z33-peptide to the preparation of non-covalent-type antibody-antimocrotubule plinabulin conjugate," 34th European Peptide Symposium 2016 & 8th International Peptide Symposium, Journal of Peptide Sci (Sep. 5, 2016—5:30pm) 22 Supplement 2 ISSN: 1099-1387 In English (Oral Presentation). Abstract.

Muller et al., 2014, Cancer chemotherapy agents target intratumoral dendritic cells to potentiate antitumor immunity, Oncoimmunology, 3(8):e954460; 4 pp.

Nabholz, 2001, Phase II study of docetaxel, doxorubiin, and cyclophosphamide as first-line chemotherapy for metastatic breast cancer, Journal of Clinical Oncology, 19:314-321.

Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," NEOPLASIA (Aug. 2013) vol. 15, No. 8, pp. 939-951.

Natoli et al., Mar. 3, 2021. Plinabulin, a distinct microtubule-targeting chemotherapy, promotes M1-like macrophage polarization and anti-tumor immunity, Frontiers in Oncology, 11:1-14.

Neidle, Stephen, ed., Cancer Drug Design and Discovery, 9th Edition, Elsevier/Academic Press, (2008) Chapter 18, pp. 427-431.

Nema et al., Excipients and Their Role in Approved Injectable Products: Current Usage and Future Directions, PDA J Pharm Sci and Tech 2011, 65 287-332.

Nereus Pharmaceuticals, Inc., Aug. 16, 2011, Phase 1/2 study of vascular disrupting agent NPI-2358 + docetaxel in patients with advanced non-small cell lung cancer, ClinicalTrials.gov, NCT00630110 <URL: https://www.clinicaltrials.gov/ct2/show/NCT00630110>.

Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.

Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.

Nielsen et al., Jun. 2005, Alternative splice variants of the human PD-1 gene, Cell Immunol., 235(2):109-116.

Niemann et al., "The Synthesis of the Three Isomeric dl-β-Pyridylalanines" Journal of the American Chemical Society, (1942) 64(7):1678-1682.

Nihei et al., "Evaluation of antivascular and antimitotic effects of tubulin binding agents in solid tumor therapy", Jpn. J. Cancer. Res. 1999, 90, 1387-1395.

Nitecki et al., "A Simple Route to Sterically Pure Diketopiperazines1," The Journal of Organic Chemistry, (1968) 33:864-866.

Ohaegbulam et al., "Human cancer immunotherapy with antibodies to the PD-1 and PD-L1 pathway," Trends Mol Med, (Oct. 30, 2014) 21(1): pp. 24-33.

Ott et al., "CTLA-4 and PD-1/PD-L1 Blockade: New Immunotherapeutic Modalities with Durable Clinical Benefit in Melanoma Patients," Clin Cancer Res (Oct. 1, 2013) 19(19): pp. 5300-5309.

Ouyang et al., Mar. 2024, Overcoming cold tumors: a combination strategy of immune checkpoint inhibors, Front. Immunol., 15: 1344272, pp. 1-8.

Oxford English Dictionary Online, 2010, Definition of prevent, http://dictionary.oed.com/, 4 pp.

Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.

Pardoll et al., "The blockade of immune checkpoints in cancer immunotherapy," Nat Rev Cancer (May 4, 2016) 12(4): 252-264.

Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, pp. 16667-16674.

Perez, Edith A., "Paclitaxel in Breast Cancer," *The Oncologist*, 1998, vol. 3, pp. 373-389.

Peters et al., Oct. 9, 2020, Schedule-dependent synergy between the histone deacetylase inhibitor belinostat and the dihydrofolate reductase inhibitor pralatrexate in T-and B-cell lymphoma cells in vitro, (Front. Cell Dev. Biol., 8:577215), pp. 1-10.

Peterson et al., 2004, Integrating pharmacology and in vivo cancer models in preclinical and clinical drug development, Eur. J. Cancer., 40:837-844.

Petrillo et al., Novel VEGF-independent strategies targeting tumor vasculature: clinical aspects, Current Pharmaceutical Design (2012), 18(19), 2702-2712.

Pettit et al. "Antineoplastic Agents. 291. Isolation and Synthesis of Combretastatins A-4, A-5, and A-6 1a." J. Med. Chem. (1995) 38: 1666-1672.

Plunkett et al., Aug. 1995, Gemcitabine: metabolism, mechanisms of action, and self-potentiation, Semin Oncol., 22(4 Suppl 11):3-10.

Prior et al., "A Comprehensive Survey of Ras Mutations in Cancer" Cancer Res. (2012) vol. 72, No. 10, pp. 2457-2467.

PRNewswire.com, Jun. 22, 2010, Nereus Pharmaceuticals completes enrollment of phase 2 advance clinical trial of plinabulin in non-small cell lung cancer, 4 pp.

Rajan et al., Dec. 2014, Nivolumab (anti-PD-1, BMS-936558, ONO-4538) in patients with advanced non-small cell lung cancer, Transl. Lung Cancer Res. 3(6):403-405.

Rathkopf, Jun. 20, 2008, Phase II trial of docetaxel with rapid androgen cycling for progressive noncastrate prostate cancer, J. Clin. Onc. 26(18):2959-2965.

Raza et al., 2014, Polymorphism: the phenomenon affecting the performance of drugs, SOJ Pharmacy & Pharmaceutical Sciences, 10 pp.

Reagan-Shaw et al., Mar. 2007, The FASEB Journal, 22:659-661.

Recht et al., May 23, 1996, The sequencing of chemotherapy and radiation therapy after conservative surgery for early-stage breast cancer, N. Engl. J. Med., 334(21):1356-6131.

Reck, M., "What future opportunities may immuno-oncology provide for improving the treatment of patients with lung cancer?" (2012) Annals of Oncology (Sep. 2012) 23 (Supp. 8) viii28-viii34.

Remington, "The Science and Practice of Pharmacy, 20th Ed" (2000) p. 709.

Rhodes, John, "Section Review: Biologicals & Immunologicals: Therapeutic potential of Schiff base-forming drugs," Expert Opinion on Investigational Drugs (1996) vol. 5, Issue 3, pp. 257-268.

Riedel et al., Jun. 2007, A phase II trial of carboplatinvinorelbine with pegfilgrastim support for the treatment of patients with advanced non-small cell lung cancer, Journal of Thoracic Oncology, 2(6):520-525.

Riemer et al., "Matching of trastuzumab (Herceptin®) epitope mimics onto the surface of Her-2/neu—a new method of epitope definition," Mol Immunol 42 (2005) pp. 1121-1124.

Roberge et al., "Antitumor Drug Fostriecin Inhibits the Mitotic Entry Checkpoint and Protein Phospatases 1 and 2A." Cancer Res. 54, 6115-21 (1994).

Roberts et al., "Trends in the Risks and Benefits to Patients with Cancer Participating in Phase 12 Clinical Trials", JAMA (2004) 292(17): 2130-2140.

Rowinsky et al, "The clinical pharmacology and use of antimicrotubule agents in cancer chemotherapeutics", Pharmacol. Ther. 1991, 52, 35-84.

Rowinsky et al. "Taxol: A Novel Investigational Antimicrotubule Agent." J. Natl. Cancer Inst. 82(15):1247-59 (1990).

Rozali et al., "Programmed Death Ligand 2 in Cancer-Induced Immune Suppression," Clinical and Developmental Immunology (2012) Article ID 656340, pp. 1-8.

Sackett, D.L. "Podophyllotoxin, Steganacin and Combretastatin: Natural Products that Bind at the Colchicine Site of Tubulin." Pharmacol. Ther. (1993) 59: 163-228.

Saito et al., "Synthesis of novel octahydro-1, 5-imino-3-benzazocin-4, 7, 10-trione derivatives having a methyl group at the C-2 position

(56) References Cited

OTHER PUBLICATIONS as ABC ring models of saframycins," Chemical & Pharmaceutical Bulletin (1997) 45(7):1120-1129.
Scholl et al., "Synthetic Lethal Interaction between Oncogenic KRAS Dependency and the STK33 Suppression in Human Cancer Cells", Cell (May 29, 2009) 137 pp. 821-834.
Schuh, 2004, Trials, tribulations, and trends in tumor modeling in mice, Toxicologic Pathology, 32(Suppl. 1):53-66.
Selby et al., Sep. 9, 2016, Preclinical development of ipilimumab and nivolumab combination immunotherapy: mouse tumor models, in vitro functional studies, and cynomolgus macaque toxicology, PloS One, 11(9):e0161779, 19 pp.
Sele et al., Jul. 2016, Novel 4-(pyrimidin-2-yl)morpholines targeting the colchicine-binding site of tubuline, Cancer Research, 76(14):abstract 1364.
Sezaki et al., "Drug Delivery Systems", Drug Development, (Jul. 1989) 13: 116, Table 2. 29.
Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.
Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.
Sherline et al. "Binding of Colchicine to Purifiied Microtubule Protein." J. Biol. Chem. 250, 5481-86 (1975).
Shi, Q et al., "Recent progress in the development of tubulin inhibitors as antimitotic antitumor agents", Curr. Pharm. Des. 1998, 4, 219-248.
Shields et al., Apr. 2023, Late-stage MC38 tumours recapitulate features of human colorectal cancer—implications for appropriate timepoint selection in preclinical studies, Front. Immunol., 14:1152035, pp. 1-23.
Singh et al., "A novel vascular disrupting agent plinabulin triggers JNK-mediated apoptosis and inhibits angiogenesis in multiple myeloma cells," Blood (2011), 117(21), 5692-5700.
Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.
Smedsgaard et al. "Using direct electrospray mass spectrometry in taxonomy and secondary metabolite profiling of crude fungal extracts." J. Microbiol. Meth. (1996) 25: 5-17.
Snegovoy AV, et al. Practical recommendations for the appointment of colony-stimulating factors in order to prevent the development of febrile neuropathy in cancer patients // Practical recommendations. Version 2016. p. 394-401.
Solter et al., Barettin, Revisited? Tetrahed Lttrs. (Mar. 2002) 43: 3385-3386.
Spain et al., Feb. 6, 2016, Management of toxicities of immune checkpoint inhibitors, Cancer Treatment Reviews, 44:51-60.
Spear et al., Vascular disrupting agents (VDA) in oncology: advancing towards new therapeutic paradigms in the clinic, Current Drug Targets (2011), 12(14), 2009-2015.
Stein, J., ed. "Internal Medicine," Fourth Edition, Mosby-Year Book, Inc., (1994), Chapters 71-72, pp. 699-729.
Stenehjem et al., "PDI/PDLI inhibitors for the treatment of advanced urothelial bladder cancer," OncoTargets and Therapy (2018) 11:5973-5989.
Steyn, P.S. "The Structures of Five Diketopiperazines from Aspergillus Ustus." Tetrahedron. 29, 107-120 (1973).
Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).
Takahashi et al. "Rhizoxin binding to tubulin at the maytansine-binding site." Biochim. Biophys. Acta. 926, 215-23 (1987).
Talmadge et al., Murine models to evaluate novel and conventional therapeutic strategies for cancer., Am J Pathol, 2007, vol. 170, Issue 3, pp. 793-804.

Tan et al., 2003, Experimental design and sample size determination for testing synergism in drug combination studies based on uniform measure, Statist. Med., 22:2091-2100.
Tang et al., Sep. 2015, What is synergy? The Saariselka agreement revisited, Front. Pharmacol., 6:181, pp. 1-5.
Thorpe, Philip E., "Vascular Targeting Agents as Cancer Therapeutics," Clinical Cancer Research, vol. 10, 415-427, Jan. 15, 2004.
Tiwari et al. "A pH- and Temperature-Dependent Cycling Method that doubles the Yield of Microtubule Protein." Anal. Biochem. 215, 96-103 (1993).
Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.
Topalian et al., "Safety, Activity, and Immune Correlates of Anti-PD-1 Antibody in Cancer," N Engl J Med. (Jun. 28, 2012) 366(26):2443-2454.
Tozer et al., Tumour vascular disrupting agents: combating treatment Resistance, British Journal of Radiology (2008), 81(Spec. Iss. 1), S12-S20.
Tsao et al., 2004, Phase I evaluation of docetaxel and topotecan for patients with advanced solid tumores, Cancer, 100:2240-2245.
Tsoumpra et al., 2015, The inhibition of human farnesyl pyrophosphate synthase by nitrogen-containing bisphosphonates. Elucidating the roes of active site threonine 201 and tyrosine 204 residues using enzyme mutants, Bone, 81:478-486.
Turner et al. "Recent Advances in the Medicinal Chemistry of Antifungal Agents." Current Pharmaceutical Design. 2, 209-224 (1996).
US Food and Drug Administration, Highlights of prescribing information, retrieved Apr. 16, 2020 from https://www.accessdata.fda.gov/drugsatfda_docs/label/2015/125031s180lbl.pdf, Rev. Nov. 2015, Reference ID:4192944.
Usui et al. "Tryprostatin A, a specific and novel inhibitor of microtubule assembly." Biochem J. 333, 543-48 (1998).
Vainas, 2012, Personalising docetaxel and G-CSF schedules in cancer patients by a clinically validated computational model, British J. Cancer, 107:814-822.
Valet et al., Dec. 2013, Challenging single- and multi-probesets gene expression signatures of pathological complete response to neoadjuvant chemotherapy in breast cancer: experience of the REMAGUS 02 phase II trial, Breast, 22(6):1052-1059.
Van der Waerden, B.L., "Wirksamkeits-und Konzentrationsbestimmung durch Tierversuche." Arch Exp Pathol Pharmakol. 195, 389-412, (1940).
Vannenman et al., Mar. 22, 2012, Combining immunotherapy and targeted therapies in cancer treatment, Nat. Rev. Cancer, 12(4):237-251.
Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).
Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.
Wailoo, 2009, The risk of febrile neutropenia in patients with non-small-cell lung cancer treated with docetaxel: a systematic review and meta-analysis, British J. Cancer 100(3):436-441.
Wang et al., 2016, The D domain of LRRC4 anchors ERK1/2 in the cytoplasm and competitively inhibits MED/ERK activation in glioma cells, Journal of Hematology & Oncology, 9:130.
Wang et al., Mar. 5, 2013, Marine-derived angiogenesis inhibitors for cancer therapy, Mar. Drugs, 11(3):903-933.
Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.
Wang, Y. et al, "Structures of a diverse set of colchicine binding site inhibitors in complex with tubulin provide a rationale for drug discovery." FEBS Journal (2016) 283, 102-111.

(56) References Cited

OTHER PUBLICATIONS

Weisenberg et al. "The Colchicine-Binding Protein of Mammalian Brain and its Relation to Microtubules." Biochemistry (1968) 7(12): 4466-79.
Weycker et al., 2019, Risk and consequences of chemotherapy-induced thrombocytopenia in US clinical practice, BMC Cancer, 19(151), 8 pp.
Wilt et al. "Anal cancer in Alaska; a retrospective study of incidence, treatment, and outcomes". Alaska Med Jul.-Sep. 2002; 44(3):56-9, 62.
Wooten et al., Jul. 29, 2021, MuSyC is a consensus framework that unifies multi-drug synergy metrics for combinatorial drug discovery, Nat. Commun., 12(1):4607, pp. 1-16).
Xi et al., 2017, RNA biomarkers: frontier of precision medicine for cancer, Non-Coding RNA, 3(1):9, 17 pp.
Yahara et al. "Microtubule Organization of Lymphocytes and its Modulation by Patch and Cap Formation." Cell. 15, 251-259 (1978).
Yamato et al., "Clinical importance of B7-H3 expression in human pancreatic cancer," British Journal of Cancer (Oct. 20, 2009) 101, pp. 1709-1716.
Yamazaki et al. "Crystal Structure and Absolute Configuration of Fumitremorgin B, a Tremorgenic Toxin from Aspergillus Fumigatus Fres." Tetrahedron Lett. 1, 27-28 (1975).
Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.
Yamori T., "A Human Cell Line Panel for Screening Anti-Cancer Drugs", Jap. J. Cancer Chemother. 24, 129-35 (1997).
Yang et al., "The *KRAS* Mutation is Highly Correlated With EGFR Alterations in Patients With Non-small Cell Lung Cancer," Fooyin J Health Sci (2009) vol. 1(2): pp. 65-71.
Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.
Yin et al., "Human Mutations That Confer Paclitaxel Resistance," Mol. Cancer Ther. vol. 9(2), pp. 327-335 (2010).
Yin et al., May 2018, Searching synergistic dose combinations for anticancer drugs, Front. Pharmacol., 9:535, pp. 1-7.
Yokio et al, "Neihumicin, A New Cytotoxic Antibiotic From Micromonospora Neihuensis," The Journal of Antibiotics, (Apr. 1988) 41(4):494-501.
Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).
Younis et al., 2011, The cost-utility of adjuvant chemotherapy using docetaxel and cylophosphamide compared with doxorubicin and cyclophosphamide in breast cancer, Current Oncology 18(8):e298-3296.
Yuan et al., 2019, Mathematical rules for synergisitc, additive, and antagonistic effects of multi-drug combinations and their application in research and development of combinatorial drugs and special medical food combinations, Food Sci. Hum. Wellness, 8:136-141.
Zacharie et al., 1997, Regioselective synthesis of 6-substituted 2-hydroxybenzaldehyde: efficient synthesis of the immunomodulator tucaresol and related analogues, Journal of the Chemical Society, 19:2925-2929.
Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.
Zheng, Lei, "Does vaccine-primed pancreatic cancer offer better candidates for immune-based therapies?" Immunotherapy (2014) 6(10):1017-1020.
Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1):19-25.
International Search Report and Written Opinion dated Jun. 21, 2022 in application No. PCT/US2022/023793.
Calculator.net, 2008, Body surface area calculator, 2 pp.
Heist et al., "Randomized phase 2 trial of plinabulin (NPI-2358) plus docetaxel in patients with advanced non-small cell lung cancer (NSCLC)." J. Clin. Oncol. (2014) vol. 32, No. 5s, (suppl; abstr 8054).
Wang et al., 2016, Third-generation inhibitors targeting EGFR T790M mutation in advanced non-small cell lung cancer, Journal of Hematology & Oncology, 9:34.
DWK Life Sciences, Sep. 24, 2021, Glass types & properties, dwkltd.com, 10 pp.
Hanggi et al., Apr. 15, 2019, Oncogenic KRAS drives immune suppression in colorectal cancer, Cancer Cell, 35:535-537.
History of changes for study: NCT03294577, Plinabulin vs. pegfilgrastim in reducing the duration of severe neutropenia in breast cancer patients receiving myelosuppressive chemotherapy with docetaxel, doxorubisin, and cyclophosphamide (TAC), Jan. 13, 2021, Clinicaltrials.gov archive, 9 pp.
Malhotra et al., 2023, Phase II trial of plinabulin in combination with nivolumab and ipilimumab in patients with recurrent small cell lung cancer (SCLC): Big Ten Cancer Research Consortium (BTCRC-LUN17-127) study, J. Immunother Cancer 11(Suppl 1):A686.
Pascolutti et al., Oct. 4, 2016, Structure and dynamics of PD-L1 and an ultra-high-affinity PD-1 receptor mutant, Structure, 24(10):1719-1728.
Remon et al., Jan. 2018, Osimertinib and other third-generation EGFR TKI in EGFR-mutant NSCLC patients, Annals of Oncology, 29(Suppl 1):i20-i27.
Smith et al., 2000, Activity of the novel immunomodulatory compound trucaresol against experimental visceral leishmaniasis, Antimicrobial Agents and Chemotherapy, 44:1494-1498.
Suzuki et al., Jan. 13, 2023, AntiPD-1 antibodies recognizing the membrane-proximal region are PD-1 agonists that can down-regulate inflammatory diseases, Sci. Immunol. 8(79):eadd4947.
Vials Direct, Mar. 26, 2020, 10ml amber glass vials open unsterile, https://web.archive.org/web/20200326000645/https://www.vialsdirect.com.au/product/10ml-amber-glass-vials-open-unsterile/, 5 pp.
Villanueva et al., Mar. 2019, A phase 1 trial combining plinabulin and nivolumab for metastatic NSCLC: trial in progress, Journal of Clinical Oncology, 37(Suppl. 8).
Wahid et al., Nov. 16, 2023, Targeting alternative splicing as a new cancer immunotherapy-phosphorylation of serine arginine-rich splicing factor (SRSF1) for SR protein kinase 1 (SP=RPK1) regulates alternative splicing of PD1 to generate a soluble antagonistic isoform that prevents T cell exhaustion, Cancer Immunol. Immunother. 72(12):4001-4014.
Xu et al., 2024, Phase 2 study of pembrolizumab (Pemb) plus plinabulin (Plin) and docetaxel (Doc) for patients with metastatic NSCLC after failure on first-line immune checkpoint inhibitor alone or combination therapy: initial efficacy and safety results on immune re-sensitization, ESMO, poster, 1 p.

\* cited by examiner

THERAPEUTIC COMPOSITIONS AND METHODS FOR TREATING CHECKPOINT INHIBITOR-RESISTANT TUMORS USING PLINABULIN-BASED COMBINATION THERAPIES

CROSS REFERENCE TO RELATED APPLICATIONS

This application is a continuation of U.S. application Ser. No. 18/554,595, filed on Oct. 9, 2023, which is the U.S. National Phase of International Application No. PCT/US2022/023793, filed Apr. 7, 2022, which claims the benefit of priority to U.S. Provisional Application No. 63/214,010, filed Jun. 23, 2021, and U.S. Provisional Application No. 63/173,015, filed Apr. 9, 2021. All of the foregoing applications are fully incorporated herein by reference in their entireties for all purposes.

FIELD OF THE DISCLOSURE

The present disclosure relates to the field of chemistry and medicine. More particularly, the present disclosure relates to compositions containing Plinabulin, and its use in treatment.

BACKGROUND

Human cancers harbor numerous genetic and epigenetic alterations, generating neoantigens potentially recognizable by the immune system (Sjoblom et al, 2006). The adaptive immune system, comprised of T and B lymphocytes, has powerful anti-cancer potential, with a broad capacity and exquisite specificity to respond to diverse tumor antigens.

Recent cancer immunotherapy research has focused substantial effort on approaches that enhance anti-tumor immunity by mediating an adaptive immune response to relevant antigens, providing specific immune-stimulatory agents such as immune checkpoint inhibitors. While cancer remains as an incurable disease for the great majority of patients, there exists a particular need for developing effective therapeutic agents and treatment regimens that can be used in cancer therapy. Patients receiving immune checkpoint inhibitors may initially respond to these checkpoint inhibitors, but at a later time become unresponsive (resistant) to these checkpoint inhibitors, or may not respond to these checkpoint inhibitors from the start of their administration ('non-responders').

SUMMARY OF THE DISCLOSURE

Some aspects described herein relate to a method of treating cancer in a subject. In some embodiments comprises administering to the subject a compound of Formula (I),

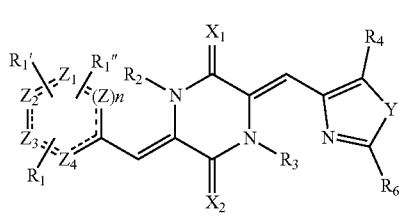

(I)

or a pharmaceutically acceptable salt thereof, wherein:
$R_1$, $R_4$, and $R_6$, are each separately selected from the group consisting of a hydrogen atom, a deuterium atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CH$_2$CO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups; $R_1'$ and $R_1''$ are each independently selected from the group consisting of a hydrogen atom, a deuterium atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl-CH$_2$CO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups; R, $R_1'$ and $R_1''$ are either covalently bound to one another or are not covalently bound to one another; $R_2$, $R_3$, and $R_5$ are each separately selected from the group consisting of a hydrogen atom, a deuterium atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups; m is an integer equal to zero, one or two; $X_1$ and $X_2$ are separately selected from the group consisting of an oxygen atom, a nitrogen atom and a sulfur atom, and Y is selected from the group consisting of a $NR_5$, an oxygen atom, a sulfur atom, a oxidized sulfur atom, a methylene group and a substituted methylene group; Z, for each separate n, if non-zero, and $Z_1$, $Z_2$, $Z_3$ and $Z_4$ are each separately selected from a carbon atom, a sulfur atom, a nitrogen atom or an oxygen atom; the dashed bonds may be either single or double bonds, wherein the cancer was resistant to prior treatment with one or more immune checkpoint inhibitor.

In some embodiments, the subject has a tumor that is resistant to immune checkpoint inhibitors. In some embodiments, the tumor that progressed after using immune checkpoint inhibitors. In some embodiments, the tumor that did not respond to checkpoint inhibitors. In some embodiments, the method further comprises administering an additional chemotherapy agent. In some embodiments, the additional chemotherapy agent is administered before administering the compound of formula (I) to the subject. In some embodiments, the additional chemotherapy agent is a taxane. In some embodiments, the taxane is docetaxel. In some embodiments, the one or more immune checkpoint inhibitor to which the subject was resistant is a PD-1 inhibitor, PD-L1 inhibitor, a CTLA-4 inhibitor, or a combination thereof. In some embodiments, the one or more immune checkpoint inhibitor to which the subject was resistant is a PD-1 inhibitor. In some embodiments, the one or more immune checkpoint inhibitor to which the subject was resistant is a PD-L1 inhibitor. In some embodiments, the one or more immune checkpoint inhibitor to which the subject was resistant is a CTLA-4 inhibitor. In some embodiments, the one or more immune checkpoint inhibitor to which the subject was resistant is pembrolizumab, nivolumab, cemiplimab, atezolizumab, avelumab, pembrolizumab, pidilizumab, ipilimumab, BMS 936559, durvalumab, spartalizumab, or any combinations thereof. In some embodiments, the one or more immune checkpoint inhibitor to which the subject was resistant is nivolumab and ipilimumab. In some embodiments, the cancer is selected from a breast cancer, a bladder cancer, a glioma, a glioblastoma, a head and neck cancer, a non-small cell lung cancer, a small cell lung cancer, recurrent small cell lung cancer (SCLC), a colorectal cancer, a gastrointestinal stromal tumor, a gastroesophageal carcinoma, a renal cell cancer, a prostate cancer, a liver cancer, a colon cancer, a pancreatic cancer, an ovarian cancer, a lymphoma, or a cutaneous T-cell lymphoma, or a melanoma. In some embodiments, the cancer is recurrent small cell lung cancer (SCLC).

In some embodiments, the method further comprises co-administering to the subject an immune checkpoint inhibitor. In some embodiments, the co-administered one or more immune checkpoint inhibitor is a PD-1 inhibitor, PD-L1 inhibitor, a CTLA-4 inhibitor, or a combination thereof. In some embodiments, the co-administered one or more immune checkpoint inhibitor is pembrolizumab, nivolumab, cemiplimab, atezolizumab, avelumab, pembrolizumab, pidilizumab, ipilimumab, BMS 936559, durvalumab, spartalizumab, or any combinations thereof. In some embodiments, the comprises administering a PD-1 antibody and a CTLA-4 antibody. In some embodiments, the PD-1 antibody is nivolumab and the CTLA-4 antibody is ipilimumab. In some embodiments, the nivolumab is administered first followed by administering ipilimumab. In some embodiments, the nivolumab is administered on the same day as ipilimumab. In some embodiments, the nivolumab and the ipilmumab are administered on the same day every two weeks. In some embodiments, of claim 21, wherein the nivolumab and the ipilmumab are administered on the same day every three weeks. In some embodiments, the nivolumab and the ipilmumab are administered on the same day every three weeks for four doses. In some embodiments, the nivolumab is administered at a range from about 100 mg to 600 mg. In some embodiments, the nivolumab is administered at a range from about 240 mg to 480 mg. In some embodiments, the co-administered one or more immune checkpoint inhibitor and the compound of Formula (I) is administered during four dosing cycles. In some embodiments, the subject receives the co-administered one or more immune checkpoint inhibitor and a compound of Formula (I) every 21-days. In some embodiments, the method further comprises administering radiation to the subject. In some embodiments, the radiation is administered before administering the compound of Formula (I) to the subject.

In some embodiments, the method further comprises administering a PD-1 or PD-L1 inhibitor and an additional chemotherapy agent to the subject. In some embodiments, further comprises administering a PD-1 or PD-L1 inhibitor and radiation to the subject. In some embodiments, the method further comprises administering a PD-1 or PD-L1 inhibitor and a CTLA-4 inhibitor to the subject. In some embodiments, the method further comprises administering a CTLA-4 inhibitor and radiation to the subject. In some embodiments, the compound of Formula (I) is administered at a dose from about 5 mg/m$^2$ to 150 mg/m$^2$. In some embodiments, the compound of Formula (I) is administered at a dose of about 20 mg/m$^2$ to about 30 mg/m$^2$. In some embodiments, the compound of formula (I) is administered orally, sublingually, buccally, subcutaneously, intravenously, intranasally, intratumorally, topically, transdermally, intradermally, intraperitoneally, intramuscularly, intrapulmonarily, vaginally, rectally, or intraocularly. In some embodiments, the compound of Formula (I) is administered on day 1 of a 14 day dosing cycle. In some embodiments, the compound of Formula (I) is administered on day 1 of a 21 day dosing cycle. In some embodiments, the compound of Formula (I) is selected from plinabulin, (3Z,6Z)-3-(phenyl-2,3,4,5,6-d$_5$)-methylene-6-((5-(tert-butyl)-1H-imidazol-4-yl)methylene)piperazine-2,5-dione; (3Z,6Z)-3-(phenyl-2,3,4,5,6-d$_5$)-methylene-d-6-((5-(tert-butyl)-1H-imidazol-4-yl)methylene)piperazine-2,5-dione; (3Z,6Z)-3-(phenylmethylene-d)-6-((5-(tert-butyl)-1H-imidazol-4-yl)methylene-d)piperazine-2,5-dione; (3Z,6Z)-3-(phenyl-2,3,4,5,6-d$_5$)-methylene-6-((5-(tert-butyl)-1H-imidazol-4-yl)methylene-d)piperazine-2,5-dione; (3Z,6Z)-3-(phenylmethylene)-6-((5-(tert-butyl)-1H-imidazol-4-yl)methylene)piperazine-2,5-dione; (3Z,6Z)-3-(phenyl-2,3,4,5,6-d$_5$)-methylene-d-6-((5-(tert-butyl)-1H-imidazol-4-yl)methylene-d)piperazine-2,5-dione; (3Z,6Z)-3-(4-Fluoro-(phenyl-2,3,5,6-d$_4$))-methylene-6-((5-(tert-butyl)-1H-imidazol-4-yl)methylene)piperazine-2,5-dione; (3Z,6Z)-3-(4-Fluoro-(phenyl-2,3,5,6-d$_4$))-methylene-6-((5-(tert-butyl)-1H-imidazol-4-yl)methylene-d)piperazine-2,5-dione; (3Z,6Z)-3-(3-fluorobenzylidene)-6-((5-(tert-butyl)-1H-imidazol-4-yl)methylene-d)piperazine-2,5-dione; (3Z,6Z)-3-(3-benzoylbenzylidene)-6-((5-(tert-butyl)-1H-imidazol-4-yl)methylene-d)piperazine-2,5-dione; (3Z,6Z)-3-(3-(4-fluorobenzoyl)benzylidene)-6-((5-(tert-butyl)-1H-imidazol-4-yl)methylene-d)piperazine-2,5-dione; (3Z,6Z)-3-(3-(4-methoxybenzoyl)benzylidene)-6-((5-(tert-butyl)-1H-imidazol-4-yl)methylene-d)piperazine-2,5-dione; (3Z,6Z)-3-(3-methoxybenzylidene)-6-((5-(tert-butyl)-1H-imidazol-4-yl)methylene-d)piperazine-2,5-dione; (3Z,6Z)-3-(3-(trifluoromethyenzydene)-6-((5-(tert-butyl)-1H-imidazol-4-yl)methylene-d)piperazine-2,5-dione; and a pharmaceutically acceptable salt thereof. In some embodiments, the compound of Formula (I) is plinabulin or a pharmaceutically acceptable salt thereof. In some embodiments, wherein a mass of the tumor is reduced from about 50% to about 100%. In some embodiments, the tumor mass is reduced from about 50% to about 70%.

Some aspects relate to a method of halting or reversing progressive cancer in a subject. In some embodiments, the method comprises administering a compound of Formula (I), wherein the subject was resistant to prior treatment with one or more immune checkpoint inhibitors. In some embodiments, the compound of Formula I is plinabulin or a pharmaceutically acceptable salt thereof. In some embodiments, the method comprises administering an additional chemotherapeutic agent to the subject. In some embodiments, the method comprises administering a PD-1 or PD-L1 inhibitor to the subject. In some embodiments, the method comprises administering a CTLA-4 inhibitor to the subject. In some embodiments, the method comprises administering radiation to the subject. In some embodiments, the method comprises administering a PD-1 or PD-L1 inhibitor to the subject. In some embodiments, the method comprises administering a CTLA-4 inhibitor to the subject. In some embodiments, the method comprises administering a PD-1 or PD-L1 inhibitor and CTLA-4 inhibitor to the subject. In some embodiments, the progressive disease is a tumor. In some embodiments, a mass of the tumor is reduced from about 50% to about 100%. In some embodiments, the tumor mass is reduced from about 50% to about 70%. In some embodiments, the radiation is administered after administering a compound of Formula (I). In some embodiments, the radiation is administered prior to administration of a compound of Formula (I). In some embodiments, the compound of Formula (I) is administered as a single dose after administering radiation. In some embodiments, wherein the compound of Formula (I) is administered in two doses after administering radiation.

DETAILED DESCRIPTION

Figure 1:
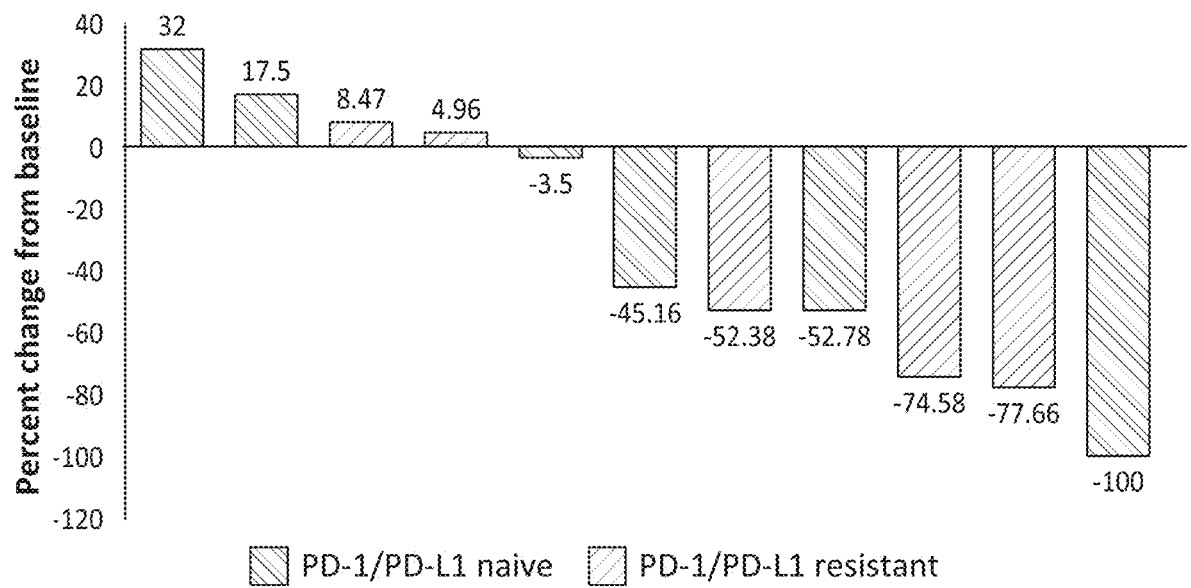
FIG. 1 illustrates a waterfall plot of best overall response in target lesions compared to baseline.

The present disclosure provides method and therapeutic compositions for reversing non-response or enhancing response to immune checkpoint inhibitor therapy for treating, ameliorating, or preventing a cancer or a tumor in a subject. In some embodiments, methods and compositions provided herein are useful in treating, delaying the progression of, preventing relapse of or alleviating a symptom of a cancer or other neoplastic condition using a compound of Formula (I). In some embodiments, the compound of Formula (I) is plinabulin. Plinabulin, (3Z,6Z)-3-Benzylidene-6-{[5-(2-methyl-2-propanyl)-1H-imidazol-4-yl]methylene}-2,5-piperazinedione, is a synthetic analog of the natural compound phenylahistin. Plinabulin can efficiently promote antigen processing and presentation by dendritic cells to effector cells, such as T-cells, and migration of dendritic cells to lymph nodes where tumor-specific antigens are presented by dendritic cells to prime immune effector cells. Exposure of dendritic cells to Plinabulin can induce maturation of dendritic cells and significantly increase their ability to prime T cells.

Some embodiments disclosed herein include administration of a compound of Formula (I) (e.g., plinabulin) to a cancer subject who initially responded to, but became refractory to prior immuno oncology therapy, for example, therapy with one or more immune checkpoint inhibitors. As described herein, it was surprisingly discovered that plinabulin can be effective against such refractory cancers.

Some embodiments disclosed herein include administration of a compound of Formula (I) (e.g., plinabulin) to a cancer subject who initially did not respond ('non-responders') to prior immuno oncology therapy, for example, therapy with one or more immune checkpoint inhibitors. As described herein, it was surprisingly discovered that adding plinabulin to checkpoint inhibitors can be effective in non-responders.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims. Methods recited herein may be carried out in any order of the recited events which is logically possible, as well as the recited order of events.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The term "agent" is used herein to denote a chemical compound, a mixture of chemical compounds, a biological macromolecule, or an extract made from biological materials.

The term "antagonist" as used herein refers to a compound that can combine with a receptor (e.g., an immune checkpoint receptor) to block a cellular activity. An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the receptor.

The term "ameliorate" as used herein refers to any reduction in the extent, severity, frequency, and/or likelihood of a symptom or clinical sign characteristic of a particular condition.

The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present disclosure may be polyclonal antibodies or monoclonal antibodies. Antibodies also include free antibodies and antigen binding fragments derived therefrom, and conjugates, e.g. pegylated antibodies, drug, radioisotope, or toxin conjugates, and the like. Monoclonal antibodies directed against a specific epitope, or combination of epitopes, will allow for the targeting and/or depletion of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like. Humanized versions of such antibodies are also within the scope of this disclosure. Humanized antibodies are especially useful for in vivo applications in humans due to their low antigenicity.

The terms "cancer", "neoplasm", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest.

The term "immune checkpoint inhibitor" as used herein refers to a molecule (e.g., small molecule, peptide, polypeptide, protein, antibody, antibody fragment and the like) that acts as an inhibitor (antagonist) of an immune checkpoint pathway. Inhibition of a pathway can include blockade of the pathway through binding to a receptor or signaling molecule that is part of the immune checkpoint pathway.

The term "polypeptide" is used herein as a generic term to refer to native protein, fragments, or analogs of a polypeptide sequence. Hence, native protein fragments, and analogs are species of the polypeptide genus.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety. The pharmaceutically acceptable excipient can be a monosaccharide or monosaccharide derivative.

The term "subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice, guinea pigs, or the like.

The terms "effective amount" or a "therapeutically effective amount" as used herein refers to an amount of a therapeutic agent that is effective to relieve, to some extent, or to reduce the likelihood of onset of, one or more of the symptoms of a disease or condition, and can include curing a disease or condition.

The terms "treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

As used herein, the term "chemotherapeutic agent" refers to an agent that reduces, prevents, mitigates, limits, and/or delays the growth of metastases or neoplasms, or kills neoplastic cells directly by necrosis or apoptosis of neoplasms or any other mechanism, or that can be otherwise used, in a pharmaceutically-effective amount, to reduce, prevent, mitigate, limit, and/or delay the growth of metastases or neoplasms in a subject with neoplastic disease. Chemotherapeutic agents include but are not limited to, for example, fluoropyrimidines; pyrimidine nucleosides; purine nucleosides; anti-folates, platinum-based agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; anti-microtubule agents; alkylating agents; antimetabolites; topoisomerase inhibitors; antivirals; and various other cytotoxic and cytostatic agents.

Compounds

In some embodiments, the compounds and therapeutic compositions for treating a cancer or tumor described herein include a compound represented by Formula (I):

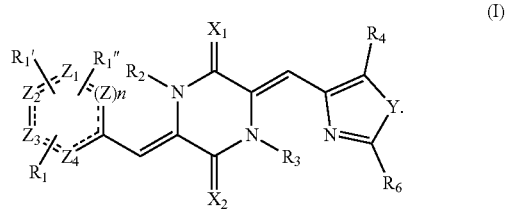

In some embodiments of Formula (I), $R_1$, $R_4$, and $R_6$, are each separately selected from the group consisting of a hydrogen atom, a deuterium atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —$CH_2CO$—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups.

In some embodiments of Formula (I), $R_1'$ and $R_1''$ are each independently selected from the group consisting of a hydrogen atom, a deuterium atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —$CH_2CO$—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups.

In some embodiments of Formula (I), R, $R_1'$ and $R_1''$ are either covalently bound to one another or are not covalently bound to one another.

In some embodiments of Formula (I), $R_2$, $R_3$, and $R_5$ are each separately selected from the group consisting of a hydrogen atom, a deuterium atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups.

In some embodiments of Formula (I), m is an integer equal to zero, one or two.

In some embodiments of Formula (I), $X_1$ and $X_2$ are separately selected from the group consisting of an oxygen atom, a nitrogen atom and a sulfur atom.

In some embodiments of Formula (I), Y is selected from the group consisting of $NR_5$, an oxygen atom, a sulfur atom, a oxidized sulfur atom, a methylene group and a substituted methylene group.

In some embodiments of Formula (I), Z, for each separate n, if non-zero, and $Z_1$, $Z_2$, $Z_3$ and $Z_4$ are each separately selected from a carbon atom, a sulfur atom, a nitrogen atom or an oxygen atom; and the dashed bonds may be either single or double bonds.

A compound of Formula (I) can be readily prepared according to methods and procedures detailed in U.S. Pat. Nos. 7,064,201 and 7,919,497, which are incorporated herein by reference in their entireties.

In some embodiments, the compounds described herein are a dehydrophenylahistin represented by Formula (II):

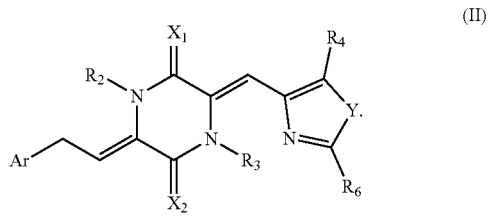

(II)

In some embodiments of Formula (II), $R_2$ and $R_3$ are each separately selected from the group consisting of a hydrogen atom; a halogen atom; mono-substituted; poly-substituted or unsubstituted, straight or branched chain variants of the following residues: $C_1$-$C_{12}$ alkyl, $C_1$-$C_{12}$ alkenyl, acyl, and alkoxy; and mono-substituted, poly-substituted or unsubstituted variants of the following residues: cycloalkyl, cycloalkoxy, aryl, heteroaryl, amino, nitro, and sulfonyl; or $R_2$ is a bond to Ar.

In some embodiments of Formula (II), $R_4$ and $R_6$ are each separately selected from the group consisting of hydrogen; halogen; hydroxyl; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, acyl, arylalkyl, heteroarylalkyl, alkyloxycarbonyloxy, ester, arylalkoxy, alkoxy, and alkylthio; mono-substituted, poly-substituted or unsubstituted variants of the following residues: acyloxy, aryloxycarbonyloxy, cycloalkyl, cycloalkenyl, cycloalkoxy, aryl, heteroaryl, aryloxy, arylcarbonyl, heterocycloalkyl, carbonyl, amino, aminocarbonyl, amide, aminocarbonyloxy, nitro, azido, phenyl, hydroxyl, thio, alkylthio, arylthio, thiooxysulfonyl, thiophene, carboxy, and cyano.

In some embodiments of Formula (II), X1 and X2 are separately selected from the group consisting of an oxygen atom, a sulfur atom, and a nitrogen atom substituted with a $R_5$ group.

In some embodiments of Formula (II), $R_5$ is selected from the group consisting of a hydrogen atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups.

In some embodiments of Formula (II), Y is selected from the group consisting of $NR_5$, an oxygen atom, a sulfur atom, an oxidized sulfur atom, a methylene group, and a substituted methylene group.

In some embodiments of Formula (II), n is 0, 1, 2, 3, or 4.

In some embodiments of Formula (II), Ar is a cyclic or polycyclic aryl or heteroaryl ring system comprising between one and three rings. In some embodiments, each ring in said system is separately a 5, 6, 7, or 8 membered ring. In some embodiments, each ring in said system separately comprises 0, 1, 2, 3, or 4 heteroatoms selected from the group consisting of oxygen, sulfur, and nitrogen. In some embodiments, each ring in said system is optionally substituted with one or more substituents selected from the group consisting of hydrogen; halogen; hydroxyl; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, acyl, arylalkyl, heteroarylalkyl, alkyloxycarbonyloxy, ester, arylalkoxy, alkoxy, and alkylthio; mono-substituted, poly-substituted or unsubstituted variants of the following residues: acyloxy, aryloxycarbonyloxy, cycloalkyl, cycloalkenyl, cycloalkoxy, aryl, heteroaryl, aryloxy, arylcarbonyl, heterocycloalkyl, carbonyl, amino, aminocarbonyl, amide, aminocarbonyloxy, nitro, azido, phenyl, hydroxyl, thio, alkylthio, arylthio, thiophene, oxysulfonyl, sulfonyl, carboxy, and cyano; and an optionally substituted fused ring selected from the group consisting of dioxole, dithiole, oxathiole, dioxine, dithiine, and oxathiine.

A compound of Formula (II) can be readily prepared according to methods and procedures detailed in U.S. Pat. Nos. 7,064,201 and 7,919,497, which are incorporated herein by reference in their entireties.

In some embodiments, a compound of Formula (I) is selected from plinabulin, (3Z,6Z)-3-(phenyl-2,3,4,5,6-$d_5$)-methylene-6-((5-(tert-butyl)-1H-imidazol-4-yl)methylene)

piperazine-2,5-dione; (3Z,6Z)-3-(phenyl-2,3,4,5,6-d$_5$)-methylene-d-6-((5-(tert-butyl)-1H-imidazol-4-yl) methylene)piperazine-2,5-dione; (3Z,6Z)-3-(phenylmethylene-d)-6-((5-(tert-butyl)-1H-imidazol-4-yl) methylene-d)piperazine-2,5-dione; (3Z,6Z)-3-(phenyl-2,3,4,5,6-d$_5$)-methylene-6-((5-(tert-butyl)-1H-imidazol-4-yl) methylene-d)piperazine-2,5-dione; (3Z,6Z)-3-(phenylmethylene)-6-((5-(tert-butyl)-1H-imidazol-4-yl) methylene-d)piperazine-2,5-dione; (3Z,6Z)-3-(phenyl-2,3,4,5,6-d$_5$)-methylene-d-6-((5-(tert-butyl)-1H-imidazol-4-yl) methylene-d)piperazine-2,5-dione; (3Z,6Z)-3-(4-Fluoro-(phenyl-2,3,5,6-d$_4$))-methylene-6-((5-(tert-butyl)-1H-imidazol-4-yl)methylene)piperazine-2,5-dione; (3Z,6Z)-3-(4-Fluoro-(phenyl-2,3,5,6-d$_4$))-methylene-6-((5-(tert-butyl)-1H-imidazol-4-yl)methylene-d)piperazine-2,5-dione; (3Z,6Z)-3-(3-fluorobenzylidene)-6-((5-(tert-butyl)-1H-imidazol-4-yl)methylene-d) piperazine-2,5-dione; (3Z,6Z)-3-(3-benzoylbenzylidene)-6-((5-(tert-butyl)-1H-imidazol-4-yl)methylene-d)piperazine-2,5-dione; (3Z,6Z)-3-(3-(4-fluorobenzoyl)benzylidene)-6-((5-(tert-butyl)-1H-imidazol-4-yl)methylene-d) piperazine-2,5-dione; (3Z,6Z)-3-(3-(4-methoxybenzoyl)benzylidene)-6-((5-(tert-butyl)-1H-imidazol-4-yl)methylene-d)piperazine-2,5-dione; (3Z,6Z)-3-(3-methoxybenzylidene)-6-((5-(tert-butyl)-1H-imidazol-4-yl)methylene-d)piperazine-2,5-dione; (3Z,6Z)-3-(3-(trifluoromethyenzydene)-6-((5-(tert-butyl)-1H-imidazol-4-yl)methylene-d)piperazine-2,5-dione; and pharmaceutically acceptable salts thereof.

In some embodiments, the compound of Formula (I) is plinabulin. In some embodiments, the compound of Formula (I) is plinabulin monohydrate. In some embodiments, the compound of Formula (I) is a salt form of plinabulin.

Immune Checkpoint Inhibitors

In some embodiments, one or more immune checkpoint inhibitor may be co-administered with a compound of Formula (I). A review describing immune checkpoint pathways and the blockade of such pathways with immune checkpoint inhibitor compounds is provided by Pardoll in Nature Reviews Cancer (April 2012), pages 252-264, which is incorporated herein by reference in its entirety. Immune check point inhibitor compounds display anti-tumor activity by blocking one or more of the endogenous immune checkpoint pathways that downregulate an anti-tumor immune response. The inhibition or blockade of an immune checkpoint pathway typically involves inhibiting a checkpoint receptor and ligand interaction with an immune checkpoint inhibitor compound to reduce or eliminate the down regulation signal and resulting diminishment of the anti-tumor response.

In some embodiments of the present disclosure, the immune checkpoint inhibitor compound inhibits the signaling interaction between an immune checkpoint receptor and the corresponding ligand of the immune checkpoint receptor. The immune checkpoint inhibitor compound can act by blocking activation of the immune checkpoint pathway by inhibition (antagonism) of an immune checkpoint receptor (some examples of receptors include CTLA-4, PD-1, LAG-3, TIM-3, BTLA, and KIR) or by inhibition of a ligand of an immune checkpoint receptor (some examples of ligands include PD-L1 and PD-L2). In such embodiments, the effect of the immune checkpoint inhibitor compound is to reduce or eliminate down regulation of certain aspects of the immune system anti-tumor response in the tumor microenvironment.

The Programmed Death 1 (PD-1) protein is an inhibitory member of the extended CD28/CTLA-4 family of T cell regulators (Okazaki et al. (2002) Curr Opin Immunol 14:391779-82; Bennett et al. (2003) J. Immunol. 170:711-8; which are incorporated herein by reference in their entirety). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

The PD-1 gene encodes a 55 kDa type I transmembrane protein (Agata et al. (1996) Int Immunol. 8:765-72, which is incorporated herein by reference in its entirety). Although structurally similar to CTLA-4, PD-1 lacks the MYPPY motif that is important for B7-1 and B7-2 binding. Two ligands for PD-1 have been identified, PD-L1 (B7-H1) and PD-L2 (B7-DC), that have been shown to downregulate T cell activation upon binding to PD-1 (Freeman et al. (2000) J. Exp. Med. 192:1027-34; Carter et al. (2002) Eur. J. Immunol. 32:634-43; which are incorporated herein by reference in their entirety). Both PD-L1 and PD-L2 are B7 homologs that bind to PD-1, but do not bind to other CD28 family members. PD-L1 is abundant in a variety of human cancers (Dong et al. (2002) Nat. Med. 8:787-9, which is incorporated herein by reference in its entirety).

PD-1 is known as an immunoinhibitory protein that negatively regulates TCR signals (Ishida, Y. et al. (1992) EMBO J. 11:3887-3895; Blank, C. et al. (Epub 2006 Dec. 29) Immunol. Immunother. 56 (5): 739-745; which are incorporated herein by reference in their entirety). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100; which are incorporated herein by reference in their entirety). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66; which are incorporated herein by reference in their entirety).

The immune checkpoint receptor cytotoxic T-lymphocyte associated antigen 4 (CTLA-4) is expressed on T-cells and is involved in signaling pathways that reduce the level of T-cell activation. It is believed that CTLA-4 can downregulate T-cell activation through competitive binding and sequestration of CD80 and CD86. In addition, CTLA-4 has been shown to be involved in enhancing the immunosuppressive activity of $T_{Reg}$ cells.

The immune checkpoint receptor programmed death 1 (PD-1) is expressed by activated T-cells upon extended exposure to antigen. Engagement of PD-1 with its known binding ligands, PD-L1 and PD-L2, occurs primarily within the tumor microenvironment and results in downregulation of anti-tumor specific T-cell responses. Both PD-L1 and PD-L2 are known to be expressed on tumor cells. The expression of PD-L1 and PD-L2 on tumors has been correlated with decreased survival outcomes.

The immune checkpoint receptor T cell membrane protein 3 (TIM-3) is expressed on Th1 and Tc1 cells, but not other T-cells. Interaction of TIM-3 with its ligand, galectin-9, produces a Th1 cell death signal. TIM-3 has been reported to play a role in maintaining T-cell exhaustion and blockade of TIM-3 has been shown to restore activity to exhausted T-cells.

The immune checkpoint receptor B- and T-lymphocyte attenuator (BTLA) receptor is expressed on both resting and activated B-cells and T-cells. Activation of BTLA when combined with its ligand HVEM (herpes virus entry mediator) results in downregulation of both T-cell activation and proliferation. HVEM is expressed by certain tumors (e.g., melanoma) and tumor-associated endothelial cells.

The immune checkpoint receptors known as killer cell immunoglobulin-like receptors (KIR) are a polymorphic family of receptors expressed on NK cells and some T-cells and function as regulators of immune tolerance associated with natural killer (NK) cells. Blocking certain KIR receptors with inhibitor compounds can facilitate the destruction of tumors through the increased activity of NK cells.

In some embodiments of the present disclosure, the immune checkpoint inhibitor compound is a small organic molecule (molecular weight less than 1000 daltons), a peptide, a polypeptide, a protein, an antibody, an antibody fragment, or an antibody derivative. In some embodiments, the immune checkpoint inhibitor compound is an antibody. In some embodiments, the antibody is a monoclonal antibody, specifically a human or a humanized monoclonal antibody.

Monoclonal antibodies, antibody fragments, and antibody derivatives for blocking immune checkpoint pathways can be prepared by any of several methods known to those of ordinary skill in the art, including but not limited to, somatic cell hybridization techniques and hybridoma, methods. Hybridoma generation is described in *Antibodies, A Laboratory Manual, Harlow and Lane*, 1988, Cold Spring Harbor Publications, New York, which is incorporated herein by reference in its entirety. Human monoclonal antibodies can be identified and isolated by screening phage display libraries of human immunoglobulin genes by methods described for example in U.S. Pat. Nos. 5,223,409, 5,403,484, 5,571, 698, 6,582,915, and 6,593,081, which are incorporated herein by reference in their entirety. Monoclonal antibodies can be prepared using the general methods described in U.S. Pat. No. 6,331,415 (Cabilly), which is incorporated herein by reference in its entirety.

As an example, human monoclonal antibodies can be prepared using a XenoMouse™ (Abgenix, Freemont, Calif.) or hybridomas of B cells from a XenoMouse. A XenoMouse is a murine host having functional human immunoglobulin genes as described in U.S. Pat. No. 6,162,963 (Kucherlapati), which is incorporated herein by reference in its entirety.

Methods for the preparation and use of immune checkpoint antibodies are described in the following illustrative publications. The preparation and therapeutic uses of anti-CTLA-4 antibodies are described in U.S. Pat. No. 7,229,628 (Allison), U.S. Pat. No. 7,311,910 (Linsley), and U.S. Pat. No. 8,017,144 (Korman), which are incorporated herein by reference in their entirety. The preparation and therapeutic uses of anti-PD-1 antibodies are described in U.S. Pat. No. 8,008,449 (Korman) and U.S. Patent Application No. 2011/0271358 (Freeman), which are incorporated herein by reference in their entirety. The preparation and therapeutic uses of anti-PD-L1 antibodies are described in U.S. Pat. No. 7,943,743 (Korman), which is incorporated herein by reference in its entirety. The preparation and therapeutic uses of anti-TIM-3 antibodies are described in U.S. Pat. No. 8,101, 176 (Kuchroo) and U.S. Pat. No. 8,552,156 (Tagayanagi), which are incorporated herein by reference in their entirety. The preparation and therapeutic uses of anti-LAG-3 antibodies are described in U.S. Patent Application No. 2011/0150892 (Thudium) and International Publication Number WO2014/008218 (Lonberg), which are incorporated herein by reference in their entirety. The preparation and therapeutic uses of anti-KIR antibodies are described in U.S. Pat. No. 8,119,775 (Moretta), which is incorporated herein by reference in its entirety. The preparation of antibodies that block BTLA regulated inhibitory pathways (anti-BTLA antibodies) are described in U.S. Pat. No. 8,563,694 (Mataraza), which is incorporated herein by reference in its entirety.

In some embodiments, the one or more immune checkpoint inhibitor is an inhibitor of PD-1, PD-L1, or CTLA-4. In some embodiments, the immune checkpoint inhibitor is a PD-1 inhibitor. In some embodiments, the immune checkpoint inhibitor is a binding ligand of PD-L1. In some embodiments, the immune checkpoint inhibitor is a PD-L1 inhibitor. In some embodiments, the immune checkpoint inhibitor is a CTLA-4 inhibitor.

In some embodiments, the one or more immune checkpoint inhibitor as described herein includes a first immune checkpoint inhibitor and a second immune checkpoint inhibitor, wherein the first immune checkpoint inhibitor is different from the second immune checkpoint inhibitor. In some embodiments, the first and the second immune checkpoint inhibitor are independently an inhibitor of PD-1, PD-L1 or CTLA-4. In some embodiments, the first immune checkpoint inhibitor is a PD-1 inhibitor, and the second immune checkpoint inhibitor is a CTLA-4 inhibitor.

In some embodiments, the immune checkpoint inhibitor is pembrolizumab, nivolumab, cemiplimab, atezolizumab, avelumab, pembrolizumab, pidilizumab, ipilimumab, BMS 936559, durvalumab, spartalizumab, or any combinations thereof. In some embodiments, the one or more immune checkpoint inhibitor may include an anti-PD-1 HuMAbs can be selected from 17D8, 2D3, 4H1, 5C4 (also referred to herein as nivolumab), 4A1 1, 7D3 and 5F4, all of which are described in U.S. Pat. No. 8,008,449, which is incorporated herein by reference in its entirety. In some embodiments, the anti-PD-1 HuMAbs can be selected from 3G10, 12A4 (also referred to herein as BMS-936559), 10A5, 5F8, 10H10, 1B12, 7H1, 1 1E6, 12B7, and 13G4, all of which are described in U.S. Pat. No. 7,943,743, which is incorporated herein by reference in its entirety.

In some embodiments, the one or more immune checkpoint inhibitor may be incorporated in a pharmaceutically acceptable formulation. In some embodiments, the one or more immune checkpoint inhibitor is incorporated in a pharmaceutically acceptable aqueous formulation. Examples of acceptable aqueous formulations include isotonic buffered and pH 4.5-8 adjusted saline solutions such as Lactated Ringer's Solution and the like.

In some embodiments, the immune checkpoint inhibitor compound is incorporated in a pharmaceutically acceptable liposome formulation, wherein the formulation is a passive or targeted liposome formulation. Examples of methods for the preparation of suitable liposome formulations of antibodies are described U.S. Pat. No. 5,399,331 (Loughrey), U.S. Pat. No. 8,304,565 (Wu) and U.S. Pat. No. 7,780,882 (Chang), which are incorporated herein by reference in their entirety.

In some embodiments, the one or more immune checkpoint inhibitor may be an antibody. In some embodiments, the antibody is a dry, lyophilized solid that is reconstituted with an aqueous reconstitution solvent prior to use. In some embodiments, the antibody is incorporated in a pharmaceutically acceptable formulation and the pharmaceutically acceptable formulation is injected directly into a tumor. In some embodiments, the immune checkpoint inhibitor antibody is incorporated in a pharmaceutically acceptable formulation and the pharmaceutically acceptable formulation is injected into the peritumoral region surrounding a tumor.

The peritumoral region may contain antitumor immune cells. In some embodiments, the antibody is incorporated in a pharmaceutically acceptable formulation and the pharmaceutically acceptable formulation is administered by intravenous injection or infusion. In some embodiments, the immune checkpoint inhibitor antibody is incorporated in a pharmaceutically acceptable formulation and the pharmaceutically acceptable formulation is administered by subcutaneous injection or intradermal injection. In some embodiments, the antibody is incorporated in a pharmaceutically acceptable formulation and the pharmaceutically acceptable formulation is administered by intraperitoneal injection or lavage.

The precise amount of immune checkpoint inhibitor compound incorporated in a particular method or therapeutic combination of the disclosure may vary according to factors known in art such as for example, the physical and clinical status of the subject, the method of administration, the content of the formulation, the physical and chemical nature of the immune checkpoint inhibitor compound, the intended dosing regimen or sequence. Those of ordinary skill in the art, however, can readily determine the appropriate amount with due consideration of such factors.

Chemotherapeutic Agents

In some embodiments, the compound of Formula (I) is co-administered with an additional chemotherapeutic agent. In some embodiments, an additional chemotherapeutic agent can be selected from the group consisting of Abiraterone, Acetate, Abitrexate (Methotrexate), Abraxane (Paclitaxel Albumin-stabilized Nanoparticle Formulation), ABVD, ABVE, ABVE-PC, AC, AC-T, ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, \Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Belcodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Cabazitaxel, Cabozantinib-S-Malate, CAF, Campath (Alemtuzumab), Camptosar (Irinotecan Hydrochloride), Capecitabine, CAPOX, Carac (Fluorouracil-Topical), Carboplatin, CARBOPLATIN-TAXOL, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cobimetinib, Cometriq (Cabozantinib-S-Malate), COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Decitabine, Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idelalisib, Ifex (Ifosfamide), Ifosfamide, IL-2 (Aldesleukin), Imatinib Mesylate, Imbruvica (Ibrutinib), Imiquimod, Imlygic (Talimogene Laherparepvec), Inlyta (Axitinib), Interferon Alfa-2b, Recombinant, Interleukin-2 (Aldesleukin), Intron A (Recombinant Interferon Alfa-2b), Iodine I 131 Tositumomab and Tositumomab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Netupitant and Palonosetron Hydrochloride, Neupogen (Filgrastim), Nexavar (Sorafenib Tosylate), Nilotinib, Ninlaro (Ixazomib Citrate), Nolvadex (Tamoxifen Citrate), Nplate (Romiplostim), Obinutuzumab, Odomzo (Sonidegib), OEPA, Ofatumumab, OFF, Olaparib, Omacetaxine Mepesuccinate, Oncaspar (Pegaspargase), Ondansetron Hydrochloride, Onivyde (Irinotecan Hydrochloride Liposome), Ontak (Denileukin Diftitox), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, Pegaspargase, Peginterferon Alfa-2b, PEG-Intron (Peginterferon Alfa-2b), Pemetrexed Disodium Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituximab, Rolapitant Hydrochloride, Romidepsin, Romiplostim, Rubidomycin (Daunorubicin Hydrochloride), Ruxolitinib Phosphate, Sclerosol Intrapleural Acrosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thioguanine, Thiotepa, Tolak (Fluorouracil-Topical), Toposar (Etoposide), Topotecan Hydrochloride, Toremifene, Torisel (Temsirolimus), Tositumomab and Iodine I 131, Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zelboraf (Vemurafenib), Zevalin (Ibritumomab Tiuxetan), Zinccard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

In some embodiments, the additional chemotherapeutic agent is docetaxel.

Radiation Therapy

In some embodiments, the compound of Formula (I) is co-administered with radiation. In some embodiments, the radiation may be selected from external beam radiation therapy or internal radiation therapy. In some embodiments, the external beam radiation therapy may be selected from three-dimensional conformal radiation therapy (3D-CRT), intensity modulated radiation therapy (IMRT), proton beam therapy, image-guided radiation therapy (IGRT), Stereotactic radiation therapy (SRT), or a combination thereof. In some embodiments, the radiation may be selected from intraoperative radiation therapy (IORT), systemic radiation therapy, radioimmunotherapy, radiosensitizers, radioprotectors, or a combination thereof.

Use and Method of Treatment

In aspects, the present disclosure provides methods and therapeutic compositions for treating, preventing, or ameliorating a cancer or tumor in a subject by administering a compound of Formula (I) (e.g., plinabulin), or a pharmaceutically acceptable salt thereof, wherein the subject was resistant to prior treatment with an immune checkpoint inhibitor. Some embodiments include identifying the subject as having been resistant to prior immune checkpoint inhibitor therapy and then administering the compound of Formula (I) (e.g., plinabulin).

In some embodiments, a method comprises treating a subject having exhibited resistance to a PD-1 inhibitor by administering a therapeutically effective amount of a compound of Formula (I). In some embodiments, a method comprises treating a subject having exhibited resistance to a PD-L1 inhibitor by administering a therapeutically effective amount of a compound of Formula (I). In some embodiments, a method comprises treating a subject having exhibited resistance to a PD-L2 inhibitor by administering a therapeutically effective amount of a compound of Formula (I). In some embodiments, a method comprises treating a subject having exhibited resistance to a CTLA-4 inhibitor by administering a therapeutically effective amount of a compound of Formula (I). In some embodiments, the method includes administering the compound of Formula (I) when the subject has exhibited resistance to two different immune checkpoint inhibitors. The two different immune inhibitors can be selected from a CTLA-4 receptor inhibitor, a PD-1 receptor inhibitor, a LAG-3 receptor inhibitor, a TIM-3 receptor inhibitor, a BTLA receptor inhibitor, a KIR receptor inhibitor a PD-L1 inhibitor or a PD-L2 inhibitor. In some embodiments, a method comprises treating a subject having exhibited resistance to a PD-1 inhibitor and CTLA-4 inhibitor by administering a therapeutically effective amount of a compound of Formula (I). In some embodiments, a method comprises treating a subject having exhibited resistance to a PD-L1 inhibitor and a CTLA-4 inhibitor by administering a therapeutically effective amount of a compound of Formula (I). In some embodiments, a method comprises treating a subject having exhibited resistance to a PD-1 inhibitor, a PD-L1 inhibitor, and a CTLA-4 inhibitor by administering a therapeutically effective amount of a compound of Formula (I).

In some embodiments, a method comprises treating a subject having exhibited resistance to a LAG-3 inhibitor by administering a therapeutically effective amount of a compound of Formula (I). In some embodiments, a method comprises treating a subject having exhibited resistance to a TIM-3 inhibitor by administering a therapeutically effective amount of a compound of Formula (I). In some embodiments, a method comprises treating a subject having exhibited resistance to a BLTA inhibitor by administering a therapeutically effective amount of a compound of Formula (I). In some embodiments, a method comprises treating a subject having exhibited resistance to a KIR inhibitor by administering a therapeutically effective amount of a compound of Formula (I). In some embodiments, the anti-KIR receptor antibody is lirilumab. In some embodiments, a method comprises treating a subject having exhibited resistance to a blocking antibody by administering a therapeutically effective amount of a compound of Formula (I). In some embodiments, the method comprises treating a subject having a tumor by administering therapeutically effective amounts of the compound of Formula (I) after a subject has failed treatment with an anti-CTLA-4 receptor antibody. In some embodiments, the anti-CTLA-4 antibody is ipilimumab or tremelimumab. In some embodiments, the method comprises treating a subject having a tumor by administering therapeutically effective amounts of the compound of Formula (I) after a subject has failed treatment with an anti-PD-1 receptor antibody. In some embodiments the anti-PD-1 antibody is cemiplimab, pembrolizumab, pidilizumab, or nivolumab.

In some embodiments, the compound of Formula (I) is co-administered with a chemotherapeutic agent. In some such embodiments, the compound of Formula (I) is administered after the chemotherapeutic agent, for example, at least 30 minutes, 1 hour, 2 hours, 4 hours, 1 day, 2 days, or 3 days after administration of the chemotherapeutic agent. In some embodiments, the chemotherapeutic agent is docetaxel. In some embodiments, the compound of Formula (I) is co-administered one or more immune checkpoint inhibitors, with or without the additional chemotherapeutic agent. In some embodiments, the compound of Formula (I) is co-administered radiation, with or without the additional chemotherapeutic agent, and with or without the one or more immune checkpoint inhibitors. In some such embodiments, the compound of Formula (I) is administered after the radiation therapy, for example, at least 30 minutes, 1 hour, 2 hours, 4 hours, 1 day, 2 days, or 3 days after administration of the radiation therapy. In some embodiments, the compound of Formula (I) may be administered with radiation on the same day that the radiation is being administered. In some embodiments, one or more immune checkpoint inhibitor may be administered prior to administration of a compound of Formula (I) and radiation. In some embodiments, one or more immune checkpoint inhibitor may be administered prior to administration of a compound of Formula (I), an additional chemotherapeutic agent, and radiation. In other embodiments, the one or more immune checkpoint inhibitor is administered after the administration of the compound of Formula (I) and the additional chemotherapeutic agent and/or radiation.

As used herein, the terms "co-administer," "co-administering," or "co-administration," refers to two or more agents or therapies that have a biological effect on a subject at the same time, regardless of when or how they are actually administered. In one embodiment, the agents or therapies are administered simultaneously. In one such embodiment, administration in combination is accomplished by combining the agents in a single dosage form. In another embodiment, the agents or therapies are administered sequentially. In some embodiments, the administration may be separated by a period of time, for example, 30 minutes, 1 hour, 2 hours, 1 day, 2 days, 3 days, or 1 week. In one embodiment the agents are administered through the same route, such as orally. In another embodiment, the agents are administered through different routes, such as one being administered orally and another being administered i.v.

In some embodiments where an immune checkpoint inhibitor is co-administered, a method for treating a subject having a cancer or tumor may include administering a therapeutically effective amount of a compound of Formula (I), or a pharmaceutically acceptable salt thereof, after the subject is administered the one or more immune checkpoint inhibitor. In some embodiments, a method of inhibiting the growth of cancer or tumor cells in a subject may include administering a therapeutically effective amount of a compound of Formula (I), or a pharmaceutically acceptable salt thereof, after the subject is administered one or more immune checkpoint inhibitor. In some embodiments, a method for increasing a cell-mediated immune response of a cell population may include administering a therapeutically effective amount of a compound of Formula (I), or a pharmaceutically acceptable salt thereof, after administering one or more immune checkpoint inhibitor.

In some embodiments, a compound of Formula (I) is co-administered with a CTLA-4 receptor inhibitor compound. In some embodiments, a compound of Formula (I) is co-administered a PD-1 or PD-L1 receptor inhibitor compound.

In some embodiments, the method comprises treating a subject by co-administering a therapeutically effective amount of a compound of Formula (I) and a LAG-3 receptor inhibitor compound. In some embodiments, the method comprises treating a subject by co-administering a therapeutically effective amount of a compound of Formula (I) and a TIM-3 receptor inhibitor compound. In some embodiments, the method comprises treating a subject by co-administering a therapeutically effective amount of a compound of Formula (I) and a BTLA receptor inhibitor compound. In some embodiments, the method comprises treating a subject by co-administering a therapeutically effective amount of a compound of Formula (I) and a KIR receptor inhibitor compound. In some embodiments, the method comprises treating a subject by co-administering a therapeutically effective amount of a compound of Formula (I) and a PD-L1 inhibitor compound. In some embodiments, the method comprises treating a subject by co-administering a therapeutically effective amount of a compound of Formula (I) and a PD-L2 inhibitor compound.

In some embodiments of the present disclosure, the method comprises treating a subject by co-administering a therapeutically effective amount of a compound of Formula (I) and a blocking antibody of an immune checkpoint pathway. In some embodiments, the method comprises treating a subject by co-administering a therapeutically effective amount of a compound of Formula (I) and an anti-CTLA-4 receptor antibody. In some embodiments, the method comprises treating a subject by co-administering a therapeutically effective amount of a compound of Formula (I) and an anti-PD-1 receptor antibody.

In some embodiments, the method comprises co-administering to a subject having a tumor a therapeutically effective amount of the compound of Formula (I) and an anti-LAG-3 receptor antibody. In some embodiments, the method comprises co-administering to a subject having a tumor a therapeutically effective amount of the compound of Formula (I) and an anti-TIM-3 receptor antibody. In some embodiments, the method comprises co-administering to a subject having a tumor a therapeutically effective amount of the compound of Formula (I) and an anti-BTLA receptor antibody. In some embodiments, the method comprises co-administering to a subject having a tumor a therapeutically effective amount of the compound of Formula (I) and an anti-KIR receptor antibody. In some embodiments, the anti-KIR receptor antibody is lirilumab. In some embodiments, the method comprises co-administering to a subject having a tumor a therapeutically effective amount of the compound of Formula (I) and an anti-PD-1 antibody. In some embodiments the anti-PD-1 antibody is cemiplimab, pembrolizumab, pidilizumab, or nivolumab. In some embodiments, the method comprises co-administering to a subject having a tumor a therapeutically effective amount of the compound of Formula (I) and an anti-PD-L1 antibody. In some embodiments, the method comprises co-administering to a subject having a tumor a therapeutically effective amount of the compound of Formula (I) and an anti-PD-L2 antibody. In some embodiments, the method comprises co-administering to a subject having a tumor a therapeutically effective amount of the compound of Formula (I) and an anti-CTLA-4 antibody. In some embodiments, the anti-CTLA-4 antibody is ipilimumab or tremelimumab.

In some embodiments, a method comprises treating a subject having exhibited resistance to one or more immune checkpoint inhibitors by co-administering a therapeutically effective amount of a compound of Formula (I) and an additional chemotherapeutic agent. In some embodiments, the additional chemotherapeutic agent is a taxane. In some embodiments, the taxane is docetaxel.

In some embodiments, a method comprises treating a subject having exhibited resistance to one or more immune checkpoint inhibitors by co-administering a therapeutically effective amount of a compound of Formula (I) and radiation therapy.

In some embodiments, a method of treating a subject with a cancer that has failed prior immune checkpoint inhibitor therapy includes administering a therapeutic combination that includes a compound of Formula (I). In some embodiments, the compound of Formula (I) is plinabulin. In some embodiments, the therapeutic combination includes an additional chemotherapeutic agent. In some embodiments, the additional chemotherapeutic agent is docetaxel. In some embodiments the therapeutic combination includes radiation. In some embodiments, the therapeutic combination includes plinabulin, a chemotherapy agent, and radiation. In some embodiments, the therapeutic combination includes plinabulin, a PD-1 or PD-L1 inhibitor, and an additional chemotherapeutic agent. In some embodiments, the therapeutic combination includes plinabulin, a PD-1 or PD-L1 inhibitor, and radiation therapy. In some embodiments, the therapeutic combination includes plinabulin, a PD-1 or PD-1 inhibitor and a CTLA-4 inhibitor. In some embodiments, the therapeutic combination includes plinabulin, a PD-1 or PD-1 inhibitor, a CTLA-4 inhibitor, and an additional chemotherapeutic agent. In some embodiments, the therapeutic combination includes plinabulin, a PD-1 or PD-1 inhibitor, a CTLA-4 inhibitor, and radiation therapy.

In some embodiments, a method for halting or reversing a progressive cancer in a subject comprising administering a compound of Formula (I). In some embodiments, the method comprises co-administering a compound of Formula (I) with one or more additional chemotherapeutic agents, one or more immune checkpoint inhibitors, and/or radiation, as described above.

In some embodiments, the present disclosure provides a method for treating breast cancer, bladder cancer, glioblastoma, metastatic brain tumor, head and neck cancer, non-small cell lung cancer, small cell lung cancer, colorectal cancer, gastrointestinal cancer, gastroesophageal cancer, renal cell cancer, prostate cancer, liver cancer, colon cancer, pancreatic cancer tumor, ovarian cancer tumor, lymphoma, cutaneous T-cell lymphoma, sarcoma, multiple myeloma, metastatic melanoma, hepatocellular carcinoma, malignant pleural mesothelioma, urothelial carcinoma, esophageal cancer, Merkel cell cancer, endometrial cancer, basal cell carcinoma or melanoma.

In some embodiments, the present disclosure provides a method for treating a solid tumor. In some embodiments, the present disclosure provides a method for treating a breast cancer tumor, a bladder cancer tumor, a glioblastoma tumor, metastatic brain tumor, a head and neck cancer tumor, a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma tumor, a cutaneous T-cell lymphoma tumor, a sarcoma tumor, a multiple myeloma tumor, metastatic melanoma tumor, hepatocellular carcinoma tumor, malignant pleural mesothelioma tumor, urothelial carcinoma tumor, esophageal cancer tumor, Merkel cell carcinoma tumor, endometrial carcinoma tumor, basal cell carcinoma tumor, or a melanoma tumor. In some embodiments, the present disclosure provides a method for treating an immune suppressed tumor. An immune suppressed tumor is a tumor that contains immune suppressive associated cells such as for example $T_{Reg}$ cells, myeloid derived suppressor cells (MDSC), M2 macrophages, and the like or immune suppressive factors such as inducible nitric oxide synthase (iNOS), PD-L1, and the like.

In some embodiments, the cancer comprises cancer cells expressing a binding ligand of PD-1. In some embodiments, the binding ligand of PD-1 is PD-L1. In some embodiments, the binding ligand of PD-1 is PD-L2.

In some embodiments, the method of treating cancer described herein further includes identifying cancer cells expressing a binding ligand of PD-1. In some embodiments, the method of treating cancer described herein further includes identifying cancer cells expressing PD-L1. In some embodiments, the method of treating cancer described herein further includes identifying cancer cells expressing PD-L2.

In some embodiments, identifying cancer cells expressing a binding ligand of PD-1 includes using an assay to detect the presence of the binding ligand. Examples of applicable assay include but are not limited to PD-L1 IHC 22C3 pharmDx kit and PD-L1 IHC 28-8 pharmDx available from Dako.

In some embodiments, the cancer comprises cancer cells expressing a binding ligand of CTLA-4. In some embodiments, the binding ligand of CTLA-4 is B7.1 or B7.2.

In some embodiments, the method of treating cancer described herein further includes identifying cancer cells expressing a binding ligand of CTLA-4. In some embodiments, the method of treating cancer described herein further includes identifying cancer cells expressing B7.1 or B7.2.

In some embodiments, the cancer is head and neck cancer, lung cancer, stomach cancer, colon cancer, pancreatic cancer, prostate cancer, breast cancer, kidney cancer, bladder cancer, ovary cancer, cervical cancer, melanoma, gliomas including glioblastoma, myeloma, lymphoma, sarcoma, multiple myeloma, or leukemia. In some embodiments, the cancer is renal cell carcinoma, malignant melanoma, non-small cell lung cancer (NSCLC), ovarian cancer, Hodgkin's lymphoma or squamous cell carcinoma. In some embodiments, the cancer is selected from breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma. In some embodiments, the cancer is a solid tumor or hematological cancer.

In some embodiments, the cancer does not have any cells expressing PD-1, PD-L1, or PD-L2 at detectable levels.

In some embodiments, the cancer is selected from breast cancer, colon cancer, glioma, metastatic brain tumor, rectal cancer, lung cancer, prostate cancer, melanoma, leukemia, ovarian cancer, gastric cancer, renal cell carcinoma, liver cancer, pancreatic cancer, lymphomas, sarcoma, multiple myeloma, and myeloma. In some embodiments, the cancer is a solid tumor or hematological cancer.

In some embodiments, the subject can be an animal, e.g., a mammal, a human. In some embodiments, the subject is a human.

In some embodiments, the compound of Formula (I) is incorporated in a pharmaceutically acceptable solution. In some embodiments, the compound of Formula (I) is incorporated in an injectable formulation. In some embodiments, the compound of Formula (I) is incorporated in an injectable formulation that substantially maintains the compound of Formula (I) at or near the injection site.

The precise amount of compound of Formula (I) incorporated in a particular method or therapeutic combination of the disclosure may vary according to factors known in art such as for example, the physical and clinical status of the subject, the method of administration, the content of the formulation, the intended dosing regimen or sequence. Accordingly, it is not practical to specifically set forth an amount that constitutes an amount of compound of Formula (I) therapeutically effective for all possible applications. Those of ordinary skill in the art, however, can readily determine an appropriate amount with due consideration of such factors.

Some embodiments relate to a method of treating cancer in a subject who exhibited resistance to checkpoint inhibitor therapy. In some embodiments, the method includes identifying a subject with a cancer that is resistant to one or more immune checkpoint inhibitor therapy, and co-administering to the subject plinabulin and one or more immune checkpoint inhibitors, wherein the one or more immune checkpoint inhibitors is an inhibitor of PD-1, PD-L1 or CTLA-4. In some embodiments, the inhibitor of PD-1 is nivolumab and is administered at 1 mg/kg. In some embodiments, the inhibitor CTLA-4 is ipilimumab and is administered at 3 mg/kg. In some embodiments, the plinabulin is administered at a dose from about 13.5 mg/m$^2$ to about 30 mg/m$^2$ on day 1 of a 21 day cycle. In some embodiments, the cancer is recurrent extensive-stage small cell lung cancer (SCLC). In some embodiments, the cancer was previously identified as unresponsive to platinum-based chemotherapy. In some embodiments, the PD-1 inhibitor and the CTLA-4 inhibitor may be administered on day 1 of a 21 day cycle. In some embodiments, the subject is administered 1, 2, 3, or 4 treatment cycles. In some embodiments, the subject may be administered 5 or more dose treatment cycles of a PD-1 inhibitor and plinabulin every two weeks.

Administration

Administration of the pharmaceutical compositions described herein can be via any of the accepted modes of administration for agents that serve similar utilities including, but not limited to, orally, sublingually, buccally, subcutaneously, intravenously, intranasally, intratumorally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

The compositions described herein may be provided in unit dosage form. As used herein, a "unit dosage form" is a composition containing an amount of a compound or composition that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, sublingual, buccal, nasal, rectal, topical (including transdermal and intradermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g. solid gel capsules and liquid gel capsules), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include additional drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. In some embodiments, excipients utilized for intravenous delivery may include Kolliphor HS 15 (polyoxyl 15 hydroxystearate or Solutol HS-15), propylene glycol and 5% dextrose in water (D5W). Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a compound of Formula (I) may be administered at a dose in the range of about 1 mg/m$^2$ to about 50 mg/m$^2$. In some embodiments, a compound of Formula (I) is administered at a dose in the range of about 1-50 mg/m$^2$ of the body surface area. In some embodiments, a compound of Formula (I) is administered at a dose in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-34.5, 27.5-32.5, 2-20, 2.5-22.5, or 9.5-21.5 mg/m$^2$, of the body surface area. In some embodiments, a compound of Formula (I) is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, a compound of Formula (I) is administered at a dose less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, a compound of Formula (I) is administered at a dose greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/m$^2$ of the body surface area.

In some embodiments, a compound of Formula (I) dose is about 5 mg-300 mg, 5 mg-200 mg, 7.5 mg-200 mg, 10 mg-100 mg, 15 mg-100 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, or about 40 mg-60 mg. In some embodiments, a compound of Formula (I) administered is about 20 mg-60 mg, 27 mg-60 mg, 20 mg-45 mg, or 27 mg-45 mg. In some embodiments, a compound of Formula (I) administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, a compound of Formula (I) dose is greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, a compound of Formula (I) dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

In some embodiments, a dose of one or more immune checkpoint inhibitors may be from about 100 μg to about 1000 mg, from about 500 μg or less to about 800 mg, from about 1.0 mg to about 600 mg, from about 100 mg to about 600 mg, or from about 200 mg to about 500 mg. In some embodiments, a dose of one or more immune checkpoint inhibitors may be from about 240 mg to about 480 mg per dose. In some embodiments, the dose of the one or more immune checkpoint inhibitors is about 240 mg. In some embodiments, the dose of the one or more immune checkpoint inhibitors is about 480 mg.

In some embodiments, one or more immune checkpoint inhibitors may be administered at a dose in the range of about 100 mg/kg to about 5000 mg/kg. In some embodiments, one or more immune checkpoint inhibitors is administered at a dose in the range of about 100-1000 mg/kg. In some embodiments, one or more immune checkpoint inhibitors is administered at a dose in the range of about 100-200, 100-300, 100-400, 100-500, 100-600, 100-700, 100-800, 100-900, 100-1000, 100-1100, 100-1200, 100-1300, 100-1375, 100-1400, 100-1500, 100-1600, 100-1700, 100-1800, 100-1900, 100-2000, 100-2250, 100-2500, 100-2750, 100-3000, 150-200, 150-300, 150-400, 150-500, 150-600, 150-700, 150-800, 150-900, 150-1000, 150-1100, 150-1200, 150-1300, 150-1375, 150-1400, 150-1500, 150-1600, 150-1700, 150-1800, 150-1900, 150-2000, 150-2250, 150-2500, 150-2750, 150-3000, 250-2000, 250-3000, 250-4000, 250-5000, 250-600, 250-700, 250-800, 250-900, 250-1000, 250-1100, 250-1200, 250-1300, 250-1375, 250-1400, 250-1500, 250-1600, 250-1700, 250-1800, 250-1900, 250-2000, 250-2250, 250-2500, 250-2750, 250-3000, 250-750, 300-400, 300-500, 300-600, 300-700, 300-800, 300-900, 300-1000, 300-1100, 300-1200, 300-1300, 300-1375, 300-1400, 300-1500, 300-1600, 300-1700, 300-1800, 300-1900, 300-2000, 300-2250, 300-2500, 300-2750, or 300-3000, mg/kg. In some embodiments, one or more immune checkpoint inhibitors is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 45, 50, 55, 60, 65, 70, 75, 80, 85, 90, 95, or 100 mg.

In some embodiments, one or more immune checkpoint inhibitor dose is about 0.5 mg-3000 mg, 0.5 mg-2500 mg, 0.5 mg-2000 mg, 0.5 mg-1500 mg, 0.5 mg-1000 mg, 0.5 mg-500 mg, 0.5 mg-200 mg, 0.75 mg-200 mg, 1.0 mg-100 mg, 1.5 mg-100 mg, 2.0 mg-100 mg, 3.0 mg-100 mg, 4.0 mg-100 mg, 1.0 mg-80 mg, 1.5 mg-80 mg, 2.0 mg-80 mg, 3.0 mg-80 mg, 4.0 mg-80 mg, 1.0 mg-60 mg, 1.5 mg-60 mg, 2.0 mg-60 mg, 3.0 mg-60 mg, or about 4.0 mg-60 mg. In some embodiments, one or more immune checkpoint inhibitors administered is about 20 mg-60 mg, 27 mg-60 mg, 20 mg-45 mg, or 27 mg-45 mg. In some embodiments, one or more immune checkpoint inhibitors administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, 52 mg-60 mg, 100 mg-200 mg, 200 mg-300 mg, 300 mg-400 mg, 400 mg-500 mg, 500 mg-1000 mg, 1000 mg-2000 mg, or 1000 mg-3000 mg. In some embodiments, one or more immune checkpoint inhibitor dose is greater than about 1 mg, 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, one or more immune checkpoint inhibitor dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg, about 300 mg, about 400 mg, about 500 mg, about 1000 mg, about 2000 mg, or about 3000 mg.

In some embodiments, the initial dose of one or more immune checkpoint inhibitor is 1 mg on day I followed a dose of a second immune checkpoint inhibitor is 3 mg.

In some embodiments, a compound of Formula (I) is administered prior to the administration of one or more immune checkpoint inhibitor. In some embodiments, a compound of Formula (I) is administered concurrently with one or more immune checkpoint inhibitor. In some embodiments, a compound of Formula (I) is administered after one or more immune checkpoint inhibitor.

In some embodiments, a compound of Formula (I) is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 24 h, 30 h, 36 h, 40 h, or 48 h after the administration of one or more immune checkpoint inhibitor. In some embodiments, a compound of Formula (I) is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 24 h, 30 h, 36 h, 40 h, or 48 h before the administration of one or more immune checkpoint inhibitor. In some embodiments, a compound of Formula (I) is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, or 48 h after the administration of one or more immune checkpoint inhibitor. In some embodiments, a compound of Formula (I) is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, or 48 h after the administration of one or more immune checkpoint inhibitor. In some embodiments, a compound of Formula (I) is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, or 48 h after the administration of one or more immune checkpoint inhibitor. In some embodiments, a compound of Formula (I) is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, or 48 h before the administration of one or more immune checkpoint inhibitor. In some embodiments, a compound of Formula (I) is administered in about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5h-1 h, 0.5 h-2 h, 0.5 h-2.5 h, 1 h-2 h, 1 h-3 h, 1 h-5 h, 1 h-24 h, 1 min-24 h, or 1 min-2 h, 1 day-2 days, 1 day-3 days, 1 day-4 days, 1 day-5 days, or 1 day-6 days after the administration of one or more immune checkpoint inhibitor. In some embodiments, a compound of Formula (I) is administered in about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h, 1 h-24 h, 1 min-24 h, or 1 min-2 h, 1 day-2 days, 1 day-3 days, 1 day-4 days, 1 day-5 days, or 1 day-6 before the administration of one or more immune checkpoint inhibitor.

In some embodiments, when a compound of Formula (I) is administered prior to one or more immune checkpoint inhibitor administration, the compound of Formula (I) is administered about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5h-1 h, 0.5 h-2 h, 0.5 h-2.5 h, 1 h-2 h, 1 h-3 h, 1 h-5 h, 1 h-24 h, 1 min-1 h, 1 min-2 h, 1 min-5 h, 1 min-24 h, 1 day-2 days, 1 day-3 days, 1 day-4 days, 1 day-5 days, or 1 day-6 days before the administration of the one or more immune checkpoint inhibitor. In some embodiments, a compound of Formula (I) is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 30 h, 36 h, 40 h, 48 h, 4 days, 5 days, 6 days, or 7 days before the administration of the one or more immune checkpoint inhibitor. In some embodiments, a compound of Formula (I) is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, 48 h, 4 days, 5 days, 6 days, or 7 days before the administration of one or more immune checkpoint inhibitor. In some embodiments, a compound of Formula (I) is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, 48 h, 3 days, 4 days, 5 days, 6 days, or 7 days before the administration of the one or more immune checkpoint inhibitor.

In some embodiments, the treatment schedule includes co-administration of one or more immune checkpoint inhibitor and a compound of Formula (I). In some embodiments, the treatment schedule includes co-administration of one or more immune checkpoint inhibitor and a compound of Formula (I) once every 1 week, 2 weeks, 3 weeks, 4 weeks, 5 weeks, 6 weeks, 7 weeks, or 8 weeks. In some embodiments, the treatment schedule includes co-administration of one or more immune checkpoint inhibitor and a compound of Formula (I) two times every 1 week, 2 weeks, 3 weeks, 4 weeks, 5 weeks, 6 weeks, 7 weeks, or 8 weeks. In some embodiments, the treatment schedule includes co-administration of one or more immune checkpoint inhibitor and a compound of Formula (I) once every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of one or more immune checkpoint inhibitor and a compound of Formula (I) twice every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of one or more immune checkpoint inhibitor and a compound of Formula (I) on day 1, day 8, and day 15 of a 21-day treatment cycle. In some embodiments, co-administration of one or more immune checkpoint inhibitor and a compound of Formula (I) includes administering one or more immune checkpoint inhibitor prior to administering plinabulin. In some embodiments, co-administration of one or more immune checkpoint inhibitor and a compound of Formula (I) includes administering one or more immune checkpoint inhibitor after administering plinabulin. In some embodiments, co-administration of one or more immune checkpoint inhibitor and a compound of Formula (I) includes administering the one or more immune checkpoint inhibitor concurrently with a compound of Formula (I). In some embodiments, one or more immune checkpoint inhibitor described in this paragraph can independently be a first, second, third, fourth, fifth, sixth, seventh, or eighth immune checkpoint inhibitor. In some embodiments, the treatment schedule includes co-administration of one or more immune checkpoint inhibitor and a compound of Formula (I) every day of the week for a week. In some embodiments, the treatment schedule includes co-administration of one or more immune checkpoint inhibitor and a compound of Formula (I) every day of the week for 2 weeks, 3 weeks, or 4 weeks. In some embodiments, the treatment schedule includes co-administration of one or more immune checkpoint inhibitor and a compound of Formula (I) on day 1 in weekly treatment. In some embodiments, the treatment schedule includes co-administration of one or more immune checkpoint inhibitor and a compound of Formula (I) on day 1 and day 2 in weekly treatment. In some embodiments, the treatment schedule includes co-administration of one or more immune checkpoint inhibitor and a compound of Formula (I) on day 1, day 2, and day 3 in weekly treatment. In some embodiments, the treatment schedule includes co-administration of one or more immune checkpoint inhibitor and a compound of Formula (I) on day 1, day 2, day 3 in weekly treatment. In some embodiments, the treatment schedule includes co-administration of one or more immune checkpoint inhibitor and a compound of Formula (I) on day 1, day 2, day 3, and day 4 in weekly treatment. In some embodiments, the treatment schedule includes co-administration of one or more immune checkpoint inhibitor and a compound of Formula (I) on day 1, day 2, day 3, day 4, and day 5 in weekly treatment. In some embodiments, the treatment schedule includes co-administration of one or more immune checkpoint inhibitor and a compound of Formula (I) on day 1, day 2, day 3, day 4, day 5, and day 6 in weekly treatment. In some embodiments, the treatment schedule includes co-administration of one or more immune checkpoint inhibitor composition and a compound of Formula (I) on day 1, day 3, and day 5 in weekly treatment. In some embodiments, the treatment cycle for the compound of Formula (I) and the one or more immune checkpoint inhibitors may be the same. In other embodiments, the treatment cycle for the compound of Formula (I) and the one or more immune checkpoint inhibitors may be different. For example, in some embodiments, the treatment cycle for the compound of Formula (I) is 21 days, whereas the treatment cycle for the one or more immune checkpoint inhibitors is 14 days. In some embodiments, one or more immune checkpoint inhibitor is used on each administration day can be the same or different. In some embodiments, one or more immune checkpoint inhibitor used on the first administration day is different from one or more immune checkpoint inhibitor used on the rest of the administration days. In some embodiments, one or more immune checkpoint inhibitor used on the first administration day is the same as or different from one or more immune checkpoint inhibitor used on the second administration day. In some embodiments, one or more immune checkpoint inhibitor used on the first administration day is the same as or different from one or more immune checkpoint inhibitor used on the third administration day. In some embodiments, one or more immune checkpoint inhibitor composition used on the first administration day is the same as or different from one or more immune checkpoint inhibitor used on the fourth administration day. In some embodiments, one or more immune checkpoint inhibitor used on the first administration day is the same as or different from one or more immune checkpoint inhibitor used on the fifth administration day. In some embodiments, one or more immune checkpoint inhibitor used on the first administration day is the same as or different from one or more immune checkpoint inhibitor used on the sixth administration day. In some embodiments, one or more immune checkpoint inhibitor used on the first administration day is the same as or different from one or more immune checkpoint inhibitor used on the seventh administration day.

In some embodiments, the treatment schedule includes administration of one or more immune checkpoint inhibitor (e.g., the first, the second, the third, the fourth, the fifth, the sixth, the seventh, or the eighth) once every 3 weeks. In some embodiments, the treatment schedule includes administration of one or more immune checkpoint inhibitor once every 1 week, 2 weeks, 3 weeks, 4 weeks, 5 weeks, 6 weeks, 7 weeks, or 8 weeks. In some embodiments, the treatment schedule includes administration of one or more immune checkpoint inhibitor two times every 1 week, 2 weeks, 3 weeks, 4 weeks, 5 weeks, 6 weeks, 7 weeks, or 8 weeks. In some embodiments, the treatment schedule includes administration of one or more immune checkpoint inhibitor once every 1 week in a treatment cycle of 1 week, 2 weeks, 3 weeks, 4 weeks, 5 weeks, 6 weeks, 7 weeks, or 8 weeks. In some embodiments, the treatment schedule includes administration of one or more immune checkpoint inhibitor twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of one or more immune checkpoint inhibitor three times (e.g., day 1, 2, 3, or day 1, 3, 5) every week in a treatment cycle of 1 week, 2 weeks, 3 weeks, 4 weeks, 5 weeks, 6 weeks, 7 weeks, or 8 weeks. In some embodiments, the treatment schedule includes administration of one or more immune checkpoint inhibitor day 1, day 8, and day 15 of a 21-day treatment cycle. The one or more immune checkpoint inhibitor described in this paragraph can independently be the first, second, third, fourth, fifth, sixth, seventh, or eighth one or more immune checkpoint inhibitor. In some embodiments, the treatment schedule includes administration of one or more immune checkpoint inhibitor every day of the week for a week. In some embodiments, the treatment schedule includes administration of the one or more immune checkpoint inhibitor every day of the week for 2 weeks, 3 weeks, or 4 weeks. In some embodiments, the treatment schedule includes administration of one or more immune checkpoint inhibitor composition on day 1 in weekly treatment. In some embodiments, the treatment schedule includes administration of one or more immune checkpoint inhibitor on day 1 and day 2 in weekly treatment. In some embodiments, the treatment schedule includes administration of one or more immune checkpoint inhibitor on day 1, day 2, and day 3 in weekly treatment. In some embodiments, the treatment schedule includes administration of one or more immune checkpoint inhibitor on day 1, day 3, day 5 in weekly treatment. In some embodiments, the treatment schedule includes administration of one or more immune checkpoint inhibitor on day 1, day 2, day 3, and day 4 in weekly treatment. In some embodiments, the treatment schedule includes administration of one or more immune checkpoint inhibitor on day 1, day 2, day 3, day 4, and day 5 in weekly treatment. In some embodiments, the treatment schedule includes administration of one or more immune checkpoint inhibitor on day 1, day 2, day 3, day 4, day 5, and day 6 in weekly treatment.

In some embodiments, the treatment schedule includes administration of a compound of Formula (I) once every 3 weeks. In some embodiments, the treatment schedule includes administration of a compound of Formula (I) once every 1 week, 2 weeks, 3 weeks, 4 weeks, 5 weeks, 6 weeks, 7 weeks, or 8 weeks. In some embodiments, the treatment schedule includes administration of a compound of Formula (I) two times every 1 week, 2 weeks, 3 weeks, 4 weeks, 5 weeks, 6 weeks, 7 weeks, or 8 weeks. In some embodiments, the treatment schedule includes administration of a compound of Formula (I) once every 1 week in a treatment cycle of 1 week, 2 weeks, 3 weeks, 4 weeks, 5 weeks, 6 weeks, 7 weeks, or 8 weeks. In some embodiments, the treatment schedule includes administration of a compound of Formula (I) twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of a compound of Formula (I) three times (e.g., day 1, 2, 3, or day 1, 3, 5) every 1 week in a treatment cycle of 1 week, 2 weeks, 3 weeks, 4 weeks, 5 weeks, 6 weeks, 7 weeks, or 8 weeks. In some embodiments, the treatment schedule includes administration of a compound of Formula (I) on day 1 of a 21-day treatment cycle. In some embodiments, the treatment schedule includes administration of a compound of Formula (I) on day 1 and day 8 of a 21-day treatment cycle. In some embodiments, the treatment schedule includes administration of a compound of Formula (I) day 1, day 8, and day 15 of a 21-day treatment cycle. In some embodiments, the treatment schedule includes administration of a compound of Formula (I) every day of the week for a week. In some embodiments, the treatment schedule includes administration of a compound of Formula (I) every day of the week for 2 weeks, 3 weeks, or 4 weeks. In some embodiments, the treatment schedule includes administration of a compound of Formula (I) on day 1 in weekly treatment. In some embodiments, the treatment schedule includes administration of plinabulin on day 1 and day 2 in weekly treatment. In some embodiments, the treatment schedule includes administration of a compound of Formula (I) on day 1, day 2, and day 3 in weekly treatment. In some embodiments, the treatment schedule includes administration of a compound of Formula (I) on day 1, day 3, day 5 in weekly treatment. In some embodiments, the treatment schedule includes administration of a compound of Formula (I) on day 1, day 2, day 3, and day 4 in weekly treatment. In some embodiments, the treatment schedule includes administration of a compound of Formula (I) on day 1, day 2, day 3, day 4, and day 5 in weekly treatment. The treatment schedule includes administration of a compound of Formula (I) on day 1, day 2, day 3, day 4, day 5, and day 6 in weekly treatment.

The treatment cycle can be repeated as long as the regimen is clinically tolerated. In some embodiments, the treatment cycle for one or more immune checkpoint inhibitor and a compound of Formula (I) is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle. In some embodiments, a new treatment cycle can occur after 1 week, 2 weeks, 3 weeks, 4 weeks, 5 weeks, 6 weeks, or 7 weeks after the completion of the previous treatment cycle.

Administration of the compositions disclosed herein can be via any of the accepted modes of administration for agents that serve similar utilities including, but not limited to, orally, subcutaneously, buccally, subcutaneously, intravenously, intranasally, intratumorally, topically, transdermally, intraperitoneally, intramuscularly, intrapulmonarilly, vaginally, rectally, intragastrically, or intraocularly. Oral and parenteral administrations are customary in treating the indications that are the subject of some embodiments.

In some embodiments, the compositions described herein can be used in combination with other therapeutic agents. In some embodiments, the compositions described herein can be administered or used in combination with treatments such as chemotherapy, radiation, and biologic therapies.

EXAMPLES

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described, and claimed herein. The reader will recognize that the skilled artisan, armed with the present disclosure, and skill in the art is able to prepare and use the disclosure without exhaustive examples.

Example 1

A Phase 3, randomized, single blinded, active-controlled trial in patients with advanced or metastatic NSCLC that has progressed after treatment with one or two, non-docetaxel containing systemic therapy regimen(s) and/or a PD-1/PD-L1 checkpoint inhibitor therapy for advanced or metastatic disease and with at least one measurable lung lesion was conducted. The study included two treatment arms: the experimental arm (docetaxel+plinabulin [DP]) and the control arm (docetaxel+placebo [D]).

On Day 1 in a 21-day cycle, all patients (in the DP and D Arms) received treatment with 75 mg/m$_2$ docetaxel administered via intravenous (IV) infusion over 1 hour (±10 minutes). On Days 1 and 8, patients randomized to DP Arm received plinabulin (diluted in D5W) therapy. On Days 1 and 8, patients randomized to D Arm received D5W. Plinabulin and D5W was administered via IV infusion over 60 minutes (±10 minutes) on Day 1 beginning 2 hours (±10 minutes) from the time the docetaxel infusion begins and again on Day 8. Dexamethasone (16 mg, 8 mg twice daily, or as per institution standard; IV or oral administration) was given the day prior to, the day of (Day 1), and the day following docetaxel infusion (Day 2). Premedication with dexamethasone was only required to be taken when docetaxel was given.

One patient in the DP arm who failed treatment with a platinum doublet and 13 cycles of anti-PD-1 therapy achieved stable disease for 29 cycles of therapy (21 day per cycle). Thus, surprisingly, docetaxel±plinabulin therapy was shown to be effective even in patients who exhibited resistance to immune checkpoint inhibitor therapy.

Example 2

In a dose-escalation Phase I study, patients with recurrent extensive-stage small cell lung cancer (SCLC) who had progressed on prior platinum-based chemotherapy were enrolled using a 3+3 design. The primary objective was to determine dose-limiting toxicities (DLT's) and recommended Phase 2 dose (RP2D). Patients were evaluable for DLT if they received at least two cycles of therapy; DLT period was defined as the first six weeks. Secondary endpoints were ORR, PFS and frequency of irAEs. Correlative analysis included inflammatory biomarkers: hsCRP, ESR, SAA and haptoglobin. The treatment schema is provided in Table 1.

TABLE 1

Treatment Schema

| Day 1, Cycles 1-4 (cycle = 21 days) | |
|---|---|
| Nivolumab | 1 mg/kg |
| Ipilimumab | 3 mg/kg |
| Plinabulin | (−1) 13.5 mg/m$^2$ |
| | (start) 20/m$^2$ |
| | (+1) 30 mg/m$^2$ |
| Day 1, Cycles 5+ (cycle = 14 days) | |
| Nivolumab | 240 mg |
| Plinabulin | As above |

Patients received nivolumab (1 mg/kg), ipilimumab (3 mg/kg) and plinabulin (as per dose escalation schema) IV on day 1 of each 21 day cycle. After completion of 4 cycles, patients continued therapy with nivolumab (240 mg) and plinabulin every 2 weeks till progression or intolerable toxicity. Patients were evaluable for DLT if they received at least 2 cycles of therapy; DLT period was defined as the first 6 weeks from C1D1.

Seventeen patients were enrolled (1 patient withdrew consent before treatment, 16 evaluable for safety). Median age was 59 years (range 43 to 78); 9 patients were male and 10 had received prior checkpoint inhibitor (CPI) therapy. Eight patients (50%) were treated at dose level 1 of plinabulin (20 mg/m2) and 8 patients at 30 mg/m2 of plinabulin (level 2); dose-level 2 was determined to be RP2D. There were 2 DLTs; 1 at level 1 (grade 3 altered mental status lasting<24 hours) and 1 at level 2 (grade 3 infusion reaction). Eight patients (50%) had at least one grade 3 or higher treatment-related AE; there were not any treatment-related deaths. The most common treatment-related AEs (all grades) were nausea (10; 63%), infusion reaction (8; 50%), vomiting (7; 44%), diarrhea (7; 44%) and fatigue (6, 32%). Seven patients (44%) had at least one ≥grade 3 treatment-related AE; there were no treatment-related deaths. Two patients (13%) had ≥grade 3 irAE requiring steroids (1 diarrhea, 1 transaminitis); both at level 1, none at level 2. At data cutoff, three patients exhibited a partial response in patients who did not receive previous checkpoint inhibitors (CPI) (3/6; 50%) and three patients in 7 evaluable patients exhibited a partial response who had exhibited progressive disease after failing prior checkpoint inhibitor (CPI) treatment (3/7; 43%). These three patients continued on treatment for 3 months, 5 months (still on treatment) and 18 months. In the three CPI-resistant patients, the tumor reduction was 52%, 75%, and 78%. The treatment-related events are further described in Table 2.

TABLE 2

| Treatment-related adverse events | | |
| --- | --- | --- |
| | All grade | ≥Grade 3 |
| Nausea | 10 (63%) | 0 |
| Infusion reaction | 8 (50%) | 1 (6%) |
| Vomiting | 7 (44%) | 0 |
| Diarrhea | 7 (44%) | 1 (6%) |
| Fatigue | 6 (32%) | 1 (6%) |
| Pyrexia | 4 (25%) | 0 |
| Rash | 3 (19%) | 0 |
| Hypertension | 3 (19%) | 1 (6%) |

FIG. 1 illustrates a waterfall plot of best overall response in target lesions compared to baseline.

Thirteen patients were evaluable for efficacy (1 withdrew consent, 1 death from unrelated cause, 1 replaced for DLT); 6 patients had PR (ORR 46%). There were 3 PRs in PD-1/PD-L1 therapy naïve patients (3/6; 50%). There were 3 PRs in PD-1/PD-L1 resistant patients (3/7; 43%). These three patients continued on treatment for 3 months, 5 months (still on treatment) and 18 months.

Figure 2A:
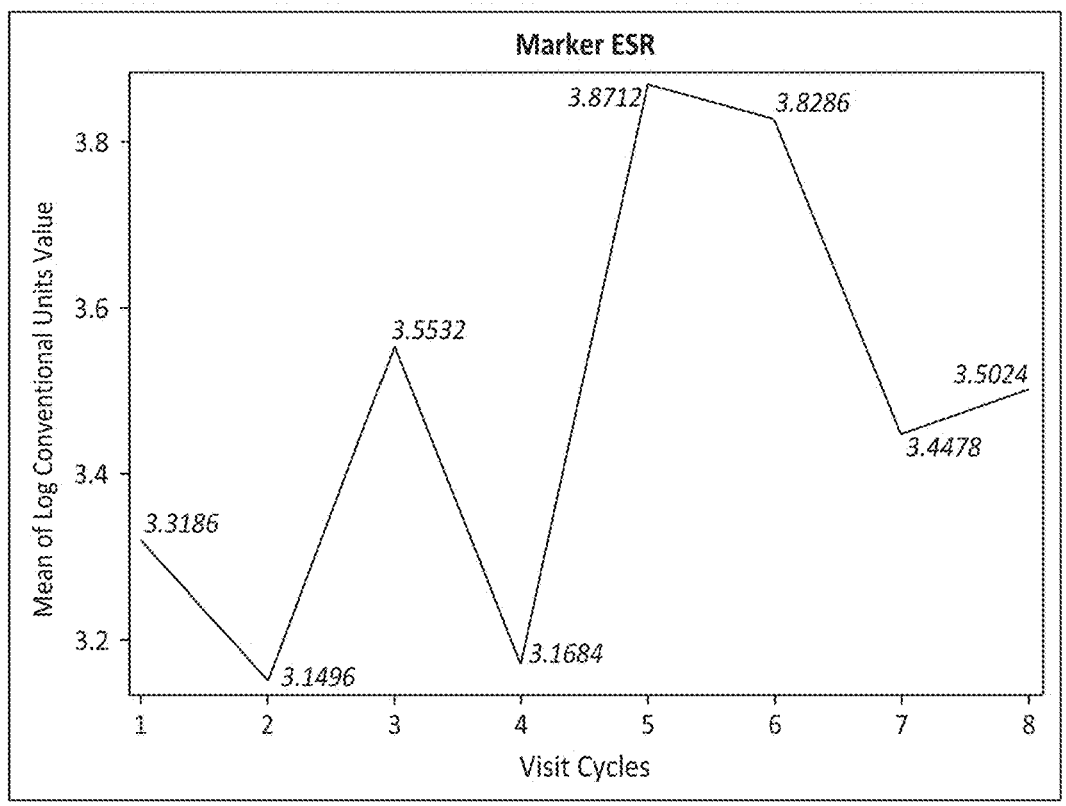
FIG. 2A illustrates the plots of log-transformed values for the mean erythrocyte sedimentation rate (ESR) at each cycle.
Figure 2B:
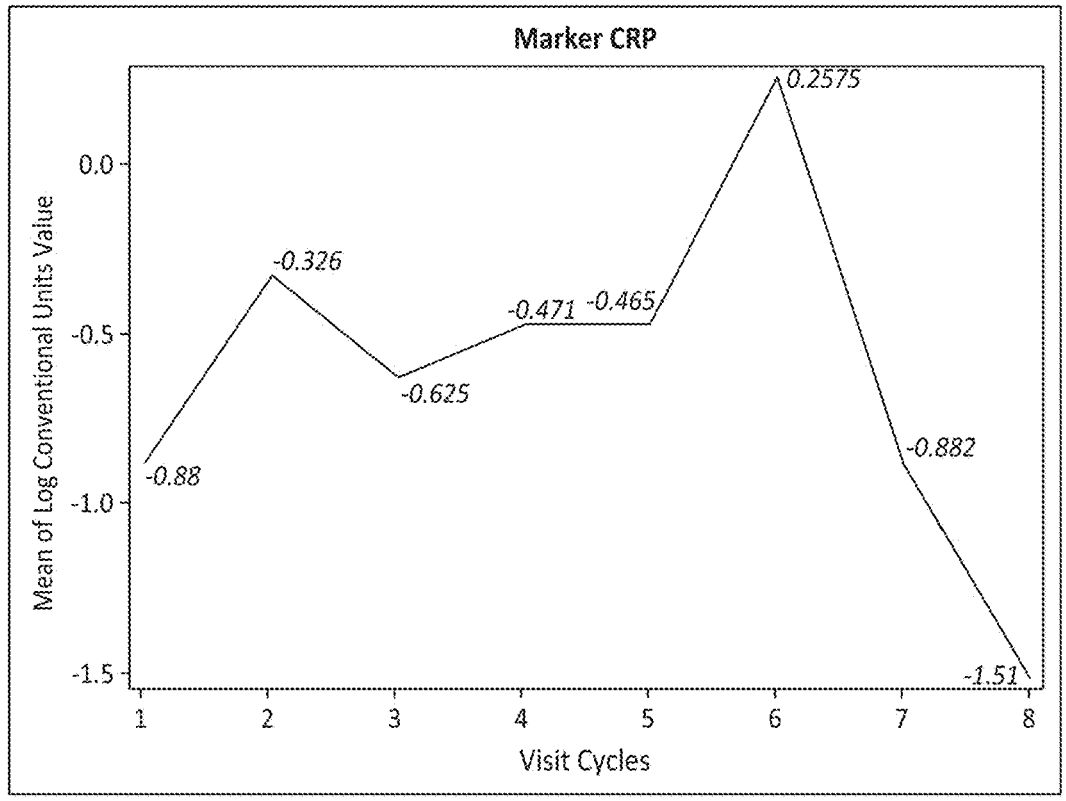
FIG. 2B illustrates the plots of log-transformed values for the mean high sensitivity C-reactive protein (CRP) at each cycle.

Levels of high sensitivity C-reactive protein [hsCRP], erythrocyte sedimentation rate [ESR] and serum amyloid A [SAA] were measured in who blood on day 1 of each cycle. FIGS. 2A and 2B illustrate the plots of log-transformed values for the mean at each cycle. Levels of hsCRP, ESR and SAA transiently increased around cycle 4 before returning to baseline values.

cancer types for this study are as follows: bladder cancer, melanoma, Merkel cell cancer, MSI-H Cancers (of any histology), non-small cell lung cancer, renal cell cancer, and small cell lung cancer.

The study cohort was tumor type specific. There were seven study cohorts from seven tumor types mentioned above for this study. Anti-PD-1/PD-L1 mAb treatment cycle was defined for the subject's treatment cycle for the study.

All subjects in Phase 1b will receive a triple combo treatment of Radiation Therapy (RT)+Plinabulin+anti-PD-1/PD-L1 mAb in Cycle 1, followed by anti-PD-1/PD-L1mAb and plinabulin combo regimen in Cycle 2 and beyond until disease progression or development of unacceptable toxicity, withdrawal from study treatment, or discontinuation of this study (see table below). A short course of local consolidative radiation therapy (RT) will be administered in Cycle 1 starting from Day 1. Optional sequential RT may be administered to target other untreated lesions at discretion of the treating doctor in Cycle 2 of any regimens. Plinabulin will be dosed on Day 1 and Day 4 of Cycle 1 of any anti-PD-1/PD-L1 regimen, and if optional RT is given in Cycle 2, Plinabulin will also be given on Day 4 of Cycle 2. Plinabulin will be given on day 1 of Cycle 3 and thereafter. Anti-PD-1/PD-L1 mAb will be dosed on Day 1 of every treatment cycle (also on Day 15 [Q4W] in case of regimen containing Avelumab or Durvalumab or Nivolumab as Anti-PD-1/PD-L1 mAb). Subjects must continue receiving the same anti-PD-1/PD-L1 mAb they failed in the prior treatment.

TABLE 3

| Phase 1b/Phase 2: Study Drugs/Regimen | | | | |
| --- | --- | --- | --- | --- |
| Phase 1b/ Phase 2: Study Drugs/ Regimen | Cycle Length | Radiation Therapy (RT) | Plinabulin 30 mg/m2 (Starting dose) or 20 mg/m2 | Anti-PD-1/ PD-L1 mAb |
| RTX + Plinabulin + Avelumab | 1 Cycle = 4 weeks | C1D1-3 (8 Gy × 3 fractions) | C1D1, 4 C2D1 C2D4 (optional if RT on C2D1) | Avelumab (800 mg): D1, 15 of every cycle |
| RTX + Plinabulin + Durvalumab | 1 Cycle = 4 weeks | or C1D1-4 (12.5 Gy × 4 fractions) | | Durvalumab (10 mg/kg): D1, 15 of every cycle |
| RTX + Plinabulin + Nivolumab | 1 Cycle = 4 weeks | or C1D1-5 (4 Gy × 5 fractions) | C3 on-ward D1 | Nivolumab (240 mg): D1, 15 of every cycle |
| RTX + Plinabulin + Atezolizumab | 1 Cycle = 3 weeks | C2D1 (optional) | | Atezolizumab (1200 mg): D1 of every cycle |
| RTX + Plinabulin + Pembrolizumab | 1 Cycle = 3 weeks | | | Pembrolizumab (200 mg): D1 of every cycle |

C = cycle, D = day, mAb = monoclonal antibody, PD = progression disease, RT = radiation therapy.

Plinabulin in combination with nivolumab and ipilimumab was safe and well tolerated. Surprisingly, plinabulin in combination with CPI therapy was shown to be effective, even in patients who exhibit resistance to CPI therapy.

Example 3

This is an open label, single-center study to assess the safety and tolerability of plinabulin when administered in combination with radiation/immunotherapy regimens in subjects with one of seven metastatic or locally advanced cancers who had disease progression on anti-PD-1/PD-L1 mAb treatment as standard of care, and to assess objective response rate of the study regimen. The seven targeted The study will begin with 30 mg/m$^2$ plinabulin in combination with a full dose of anti-PD-1/PD-L1 mAb and RT. A lower dose level at 20 mg/m$^2$ of plinabulin will be explored as necessary depending on observed toxicity. Anti-PD-1 or PD-L1 antibody dose according to FDA drug inserts will not change in phase 1b.

Once a minimum toxicity dose (MTD) is determined, an additional 10 patients will be enrolled for additional experience with safety and efficacy in each of the seven cancer type cohort and to determine the recommended phase 2 dose (RP2D). The RP2D will be selected based on both safety and totality of clinical evidence (e.g., PK/PD data), and is not necessarily the MTD. Patients treated at the MTD/RP2D in the dose finding will roll over into the cohort expansion.

Anti-PD-1/PD-L1 mAb dose will follow FDA recommendations to each indication and will not change in the expansion.

Phase 2:

Subjects with the selected tumor type will be accrued to receive the plinabulin MTD/RP2D in combination with RT and anti-PD-1/PD-L1 mAb. Anti-PD-1/PD-L1 mAb dose will follow FDA recommendations to each indication and will not change in the study. They will be randomized to one of two treatment arms in a 1:1 ratio. The randomization will be stratified by the number of mets (oligo (<=3 vs >3) and ECOG 0-1 vs 2.

Arm A: Radiation Therapy+Plinabulin+anti-PD-1/PD-L1 mAb (experimental)

Arm B: Radiation Therapy+anti-PD-1/PD-L1 mAb (control)

Subjects in arm A will receive triple combo in Cycle 1, followed by plinabulin and anti-PD-1/PD-L1 mAb double combo for Cycle 2 and beyond (see table below).

Subjects in arm B will receive combo regimen of RT and anti-PD-1/PD-L1 mAb in Cycle 1, followed by anti-PD-1/PD-L1 mAb alone for Cycle 2 and beyond (see table below).

Treatment will continue until disease progression, development of unacceptable toxicity, withdrawal from study treatment, or discontinuation of this study. Because the experimental combination arm is not expected to be worse than the control arm, no futility monitoring is planned.

A short course of local consolidative RT will be administered in Cycle 1 starting from Day 1. An optional sequential RT to other untreated lesions at discretion of the treating doctor is allowed (Cycle 2 Q4W; Cycle 2 Q3W). Plinabulin will be dosed on Day 1 of every treatment cycle and/or anti-PD-1/PD-L1 mAb will be dosed on Day 1 of every treatment cycle ((also on Day 15 [Q4W] in case of regimen containing Avelumab or Durvalumab or Nivolumab as Anti-PD-1/PD-L1 mAb) to subjects based on their treatment assignment.

For subjects in Phase 1b and Phase 2, toxicity will be managed by treatment interruption, dose reduction and/or treatment discontinuation in accordance with prespecified dose modification instructions.

Radiation Therapy (RT) Administration. Radiation therapy will be delivered using external beam radiation, with either 2D/conventional techniques, three-dimensional conformal therapy, intensity modulated radiation therapy (IMRT), stereotactic radiosurgery (SRS) or proton beam therapy (PBT), at the discretion of the treating radiation oncologist.

Radiation Therapy (RT) will be administered with one of three regimens: 8 Gy×3 fractions, 12.5 Gy×4 fractions, and/or 4 Gy×5 fractions from Days 1 to 3 (3 fractions), Days 1 to 4 (4 fractions), or Days 1 to 5 (5 fractions) in Cycle 1. The choice of RT regimens for tumors and lesions is at the discretion of the treating radiation oncologist. RT will target up to a maximum of 5 tumor lesions, and any of the radiation regimens could be use simultaneously or sequentially. Optional sequential RT is at the discretion of the treating radiation oncologist is warranted to target other untreated lesions with same regimens described above (Cycle 2 Q4W; Cycle 2 Q3W). Treatment can be for any lesions in nodes and organs including brain and bone. At least one measurable lesion will be left untreated for disease assessment during the study. Assessment of responses however are not reliant on RT treated tumor lesions and bony lesions. Brain metastasis are treated and not be used for irRECIST response assessment.

If patients develop toxicity attributable to radiation after receiving at least one dose of radiation, the rest of the radiation treatment may be discontinued, and the AEs will be documented. Since the number of fractions are between 3-5 fractions, patients could receive at least 1 fraction up to 5 fractions. The initially prescribed dose per fraction will not change, but it is possible to simply reduce the total dose delivered. The patient will have a visit with the treating radiation oncologist at the end of every cycle of radiation treatment.

PD-1 or PD-L1 Administration: Subjects are given the same anti-PD-1/PD-L1 mAb on which they have failed in prior treatment. Anti-PD-1/PD-L1 mAb are dosed according to FDA recommendations as specified under Phase 1b and Phase 2 above. Anti-PD-1/PD-L1 mAb treatment cycle will

TABLE 4

Phase 2 Only: Study Drugs/Regimen

| Phase 2 only: Study Drugs/Regimen | Cycle Length | Radiation Therapy (RT) | Plinabulin 30 mg/m2 (Starting dose) or 20 mg/m2 | Anti-PD-1/PD-L1 mAb |
|---|---|---|---|---|
| RTX + Avelumab | 1 Cycle = 4 weeks | C1D1-3 (8 Gy × 3 fractions) | N/A[a] | Avelumab (800 mg): D1, 15 of every cycle |
| RTX + Durvalumab | 1 Cycle = 4 weeks | or C1D1-4 (12.5 Gy × 4 fractions) | | Durvalumab (10 mg/kg): D1, 15 of every cycle |
| RTX + Nivolumab | 1 Cycle = 4 weeks | or C1D1-5 (4 Gy × 5 fractions) | | Nivolumab (240 mg): D1, 15 of every cycle |
| RTX + Atezolizumab | 1 Cycle = 3 weeks | C2D1 (optional) | | Atezolizumab (1200 mg): D1 of every cycle |
| RTX + Pembrolizumab | 1 Cycle = 3 weeks | | | Pembrolizumab (200 mg): D1 of every cycle |

C = cycle, D = day, mAb = monoclonal antibody, N/A = not applicable, PD = progression disease, RT = radiation therapy.
[a]Plinabulin marked N/A only applies to Arm B for phase 2, not arm A. Plinabulin will be administered to subjects in Arm A on days listed in Phase 1b/Phase 2: Study Drugs/Regimen table above.

define subject's treatment cycle for the study. The list of anti-PD-1/PD-L1 mAb approved to date for the following indications is provided here:

Merkel cell cancer: Avelumab, Pembrolizumab, Renal Cell Cancer: Pembrolizumab, Nivolumab, Bladder cancer: Durvalumab, MSI-H cancers (of any histology): Pembrolizumab, Nivolumab, Non-small cell lung cancer: Pembrolizumab, Nivolumab, Atezolizumab, Durvalumab, Small Cell lung cancer: Pembrolizumab, Nivolumab, Atezolizumab, Melanoma: Nivolumab or Pembrolizumab single agent.

Any approved anti-PD-1/PD-L1 mAb can be used for the study. Anti-PD-1/PD-L1 mAb dose and administration route: Avelumab 800 mg IV over 1 hr on Day 1 and Day 15 in Q4W, Atezolizumab 1200 mg Q3W IV 1 hr in $1^{st}$ dose, may infuse over 30 min in subsequent doses if tolerated well, Durvalumab 10 mg/kg IV over 1 hr on Day 1 and Day 15 in Q4W, Nivolumab 240 mg IV over 30-60 min on Day 1 and Day 15 in Q4W, Pembrolizumab 200 mg Q3W IV over 30 min. Anti-PD-1/PD-L1 mAb will be administered after the rest period (at least 3 hours, but no later than 12 hours) of RT, if applicable, and before plinabulin infusion. The FDA product insert will be followed for the instructions of treatment dosing and toxicity management of each approved anti-PD-1 or PD-L1 mAb.

Plinabulin Administration. Plinabulin will be administered on Day 1 and Day 4 in Cycle 1 intravenously, and if optional RT is given in Cycle 2, Plinabulin will also be given on Day 1 and Day 4 of Cycle 2. Optional RT will always be given in Cycle 2 on Day 1. Plinabulin will always be given on day 1 of Cycle 3 and after.

Two plinabulin dose levels may be explored in phase 1b trial. Plinabulin dose level at 30 mg/m$^2$ will be first tested in phase 1b trial. If it is not deemed tolerable, then the dose at 20 mg/m$^2$ will be explored.

For plinabulin at 30 mg/m$^2$ dose level a 60-minute infusion through IV with ±10 min window is recommended. For plinabulin at 20 mg/m$^2$ dose level a 30-minute infusion through IV with ±5 min window is recommended. For patients with a body surface area (BSA) greater than 2.4 m$^2$, dosing is calculated using the maximum BSA of 2.4 m$^2$ for Plinabulin.

Plinabulin is administered at 1-2 hours after completion of anti-PD-1 or PD-L1 mAb infusion when applicable, or at least 3 hours (but not longer than 12 hours) after the radiotherapy.

Safety & Efficacy Assessments. Safety and tolerability are assessed throughout the study according to NCI-CTCAE version 5.0. Vital signs, physical examination, and safety lab test result review (hematology, chemistry & urinalysis) will have to be performed prior to the study treatment to make sure the study treatment is safe to be administered.

Tumor assessments will be performed by the investigators based on both immune-related Response Evaluation Criteria In Solid Tumors (irRECIST) and modified Response Evaluation Criteria In Solid Tumors (RECIST) 1.1. Treatment decisions by the investigator will be based on irRECIST.

Tumor assessments will be carried out during the Screening, and every 9 weeks (±1 week) for 27 weeks (during Q3W dosing) or every 8 weeks (±1 week) for 24 weeks (during Q4W dosing), then every 12 weeks during treatment cycles in the Treatment Phase regardless of treatment cycles and follow up period. Computed tomography (CT)/magnetic resonance imaging (MRI) scans of chest, abdomen, and pelvis and of other known sites of disease will be obtained at Screening (within 28 days prior to Cycle 1/ Day 1), at all tumor assessment time points, and as indicated clinically. RT treated lesions will not be used for response assessment. At least one measurable tumor lesion will be kept untreated by RT for disease response assessment across the treatment.

Subjects going off treatment without disease progression will also undergo tumor assessments per the Schedule of Procedures/Assessments until disease progression is documented or another anticancer therapy is initiated.

If the time point tumor assessment is progressive disease (PD), treatment will continue, and tumor assessments repeated at least 4 weeks later in order to confirm immune-related progressive disease (irPD).

Study Population: Advanced staged cancer subjects who are either unresponsive or relapsed following prior standard PD-1 or PD-L1 regimen±chemotherapy or anti-CTLA4, for one of the following seven cancers: non-small cell lung cancer, small cell lung cancer, renal cell cancer, bladder cancer, Merkle cell cancer, MSI-H cancer (any history), and melanoma.

Treatment Duration: Treatment will continue until disease progression, development of unacceptable toxicity (i.e., DLTs), withdrawal from study treatment, or discontinuation of this study.

Duration of Study: Screen period: up to 28 days. Treatment period: Study treatment continues until disease progression (estimate 2-6 months), development of unacceptable toxicity, withdrawal from study treatment, or discontinuation of this study. Follow-up period: Study Follow-up consists of the End of Treatment Visit and the Follow-up Visits. The End of Treatment Visit will occur within 30 days following the last dose of study treatment, then transit to the Follow-up visit period. The Follow-up Visit at every 12 weeks (±1 week) continue as long as the study subject is alive unless the subject withdraws consent or until the sponsor terminates the study. In the Follow-up Period, Subjects who discontinued for reasons other than progression of disease (and withdrawal from study treatment) will continue to visit the clinic for study assessments and evaluation of their disease by CT, MRI, or positron emission tomography (PET)/CT scan approximately every 12 weeks until progression of disease is determined, the patient receives additional antineoplastic medication, or for a maximum of 5 years Subjects who stopped treatment due to disease progression will be followed up for survival status.

What is claimed is:

1. A method of treating cancer resistant to or progressed after prior treatment with one or more immune checkpoint inhibitor, the method comprising:
    identifying a subject as having been resistant to or progressed after prior treatment with a PD-1 or PD-L1 inhibitor;
    administering to the subject a PD-1 or PD-L1 inhibitor; and
    administering to the subject plinabulin.

2. The method of claim 1, wherein the PD-1 or PD-L1 inhibitor administered to the subject is selected from the group consisting of pembrolizumab, nivolumab, cemiplimab, atezolizumab, avelumab, pembrolizumab, pidilizumab, BMS 936559, durvalumab, spartalizumab, and combinations thereof.

3. The method of claim 2, wherein the PD-1 or PD-L1 inhibitor administered to the subject is pembrolizumab or nivolumab.

4. The method of claim 1, wherein the PD-1 or PD-L1 inhibitor administered is a monoclonal antibody.

5. The method of claim 1, wherein the cancer is selected from the group consisting of head and neck cancer, lung cancer, stomach cancer, colon cancer, pancreatic cancer, prostate cancer, breast cancer, kidney cancer, bladder cancer, cervical cancer, melanoma, gliomas, myeloma, lymphoma, sarcoma, multiple myeloma, leukemia, renal cell carcinoma, malignant melanoma, non-small cell lung cancer (NSCLC), ovarian cancer, Hodgkin's lymphoma, squamous cell carcinoma, rectal cancer, gastric cancer, and liver cancer.

6. The method of claim 1, wherein the cancer is selected from the group consisting of breast cancer, bladder cancer, glioblastoma, metastatic brain tumor, head and neck cancer, non-small cell lung cancer, small cell lung cancer, colorectal cancer, gastrointestinal cancer, gastroesophageal cancer, renal cell cancer, prostate cancer, liver cancer, colon cancer, pancreatic cancer tumor, ovarian cancer, lymphoma, cutaneous T-cell lymphoma, sarcoma, multiple myeloma, metastatic melanoma, hepatocellular carcinoma, malignant pleural mesothelioma, urothelial carcinoma, esophageal cancer, Merkel cell cancer, endometrial cancer, basal cell carcinoma, and melanoma.

7. The method of claim 1, wherein the cancer is selected from the group consisting of head and neck cancer, non-small cell lung cancer, small cell lung cancer, gastrointestinal cancer, Hodgkin's lymphoma, and breast cancer.

8. The method of claim 1, wherein the cancer is selected from the group consisting of head and neck cancer, non-small cell lung cancer, small cell lung cancer, urothelial carcinoma, colorectal cancer, renal cell carcinoma, gastric cancer, esophageal cancer, cervical cancer, liver cancer, hepatocellular carcinoma, Merkel cell cancer, squamous cell carcinoma, endometrial cancer, melanoma, and breast cancer.

9. The method of claim 1, wherein the cancer is non-small cell lung cancer.

10. The method of claim 1, further comprising administering a chemotherapeutic agent to the subject.

11. The method of claim 10, wherein the chemotherapeutic agent is docetaxel.

12. The method of claim 10, wherein the chemotherapeutic agent is a platinum-based agent.

13. The method of claim 12, wherein the platinum-based agent is selected from the group consisting of oxaliplatin, carboplatin, and cisplatin.

14. The method of claim 1, wherein said administration comprises a treatment cycle that is repeated multiple times.

15. The method of claim 14, wherein each treatment cycle comprises:
administering to the subject a PD-1 or PD-L1 inhibitor on Day 1; and
administering plinabulin to the subject on Day 1.

16. The method of claim 15 wherein each treatment cycle further comprises administering docetaxel to the subject on Day 1.

17. The method of claim 14, wherein the PD-1 or PD-L1 inhibitor is pembrolizumab, each dose of pembrolizumab inhibitor administered is about 200 mg, and each dose of plinabulin administered is about 30 mg/m$^2$.

18. The method of claim 14, wherein each treatment cycle is 14 days long.

19. The method of claim 14, wherein each treatment cycle is 21 days long.

20. The method of claim 1, wherein the dose of plinabulin administered is about 30 mg/m$^2$.

21. The method of claim 1, wherein the PD-1 or PD-L1 inhibitor is pembrolizumab and the dose of pembrolizumab administered is about 200 mg.

22. The method of claim 1, further comprising administering radiation to the subject.

* * * * *